United States Patent
Khang et al.

(10) Patent No.: US 9,981,042 B2
(45) Date of Patent: May 29, 2018

(54) CARBON NANOTUBE-BASED ANTI-CANCER AGENT CAPABLE OF SUPPRESSING DRUG RESISTANCE

(71) Applicant: INDUSTRY-ACADEMIC COOPERATION FOUNDATION GYEONGSANG NATIONAL UNIVERSITY, Jinju-si, Gyeongsangnam-do (KR)

(72) Inventors: Dong Woo Khang, Jinju-si (KR); Sang Soo Kang, Jinju-si (KR); Jungil Choi, Jinju-si (KR); Tae Hyun Nam, Jinju-si (KR)

(73) Assignee: INDUSTRY-ACADEMIC COOPERATION FOUNDATION GYEONGSANG NATIONAL UNIVERSITY, Jinju-si, Gyeongsangnam-Do (KR)

( * ) Notice: Subject to any disclaimer, the term of this patent is extended or adjusted under 35 U.S.C. 154(b) by 2 days.

(21) Appl. No.: 14/422,584

(22) PCT Filed: Aug. 23, 2013

(86) PCT No.: PCT/KR2013/007595
§ 371 (c)(1),
(2) Date: Feb. 23, 2015

(87) PCT Pub. No.: WO2014/030974
PCT Pub. Date: Feb. 27, 2014

(65) Prior Publication Data
US 2015/0196650 A1    Jul. 16, 2015

(30) Foreign Application Priority Data

Aug. 23, 2012 (KR) .................. 10-2012-0092644

(51) Int. Cl.
*A61K 47/50* (2017.01)
*A61K 47/48* (2006.01)
(Continued)

(52) U.S. Cl.
CPC ...... *A61K 47/48015* (2013.01); *A61K 9/0019* (2013.01); *A61K 9/0092* (2013.01);
(Continued)

(58) Field of Classification Search
None
See application file for complete search history.

(56) References Cited

U.S. PATENT DOCUMENTS

2009/0087493 A1* 4/2009 Dai ............... A61K 9/0092
424/490
2010/0021471 A1* 1/2010 Chen ............... A61K 9/0019
424/141.1
(Continued)

FOREIGN PATENT DOCUMENTS

KR    10-2011-0096641 A    8/2011

OTHER PUBLICATIONS

Wenping, Wang, Masters thesis of Gyeongsang National Univeristy, Anticancer loaded multi-walled carbon nanotube for targeting tumors, Aug. 2011.*

(Continued)

*Primary Examiner* — Robert A Wax
*Assistant Examiner* — Melissa S Mercier
(74) *Attorney, Agent, or Firm* — Lucas & Mercanti, LLP

(57) ABSTRACT

The present invention provides an anticancer agent comprising a multi-walled carbon nanotube and an anticancer drug covalently attached to the surface of the multi-walled carbon nanotube, in order to anticancer agent capable of solving drug resistance problem.

14 Claims, 22 Drawing Sheets

(51) Int. Cl.
  *A61K 33/44* (2006.01)
  *A61K 9/00* (2006.01)
  *A61K 31/155* (2006.01)
  *A61K 31/282* (2006.01)
  *A61K 31/407* (2006.01)
  *A61K 31/704* (2006.01)
  *A61K 33/24* (2006.01)
  *A61K 38/18* (2006.01)
  *A61K 47/69* (2017.01)

(52) U.S. Cl.
  CPC .......... *A61K 31/155* (2013.01); *A61K 31/282* (2013.01); *A61K 31/407* (2013.01); *A61K 31/704* (2013.01); *A61K 33/24* (2013.01); *A61K 33/44* (2013.01); *A61K 38/1808* (2013.01); *A61K 47/6921* (2017.08); *A61K 47/6929* (2017.08); *Y10T 428/2982* (2015.01)

(56) References Cited

U.S. PATENT DOCUMENTS

2013/0183354 A1* 7/2013 Harrison, Jr. ...... A61K 41/0057
  424/400

2014/0199240 A1* 7/2014 Zeevaart ............... C07F 9/386
  424/1.77

OTHER PUBLICATIONS

Perez et al. (Paclitaxel in Breast Cancer, accepted Sep. 2, 1998).*
Gao et al. (Covalent Immobilization of Proteins on Carbon Nanotubes Using the Cross linker 1-ethyl-3-(3-dimethylaminopropyl)carbodiimide—a Critical Assessment, Aug. 29, 2008).*
Wenping Wang; Master's thesis of Gyeongsang National University; Anticancer loaded multi-wall carbon nanotube for targeting tumors; Aug. 2011.
Seyed Yazdan Madani, et al; A new era of cancer treatment: carbon nanotubes as drug delivery tools; International Journal of Nanomedicine; vol. 6; 2011; pp. 2963-2979.
L.E. Murr; Microstructures and Nanostructures for Environmental Carbon Nanotubes and Nanoparticulate Soots; Int. J. Environ. Res. Public Health; 5(5); 2008; pp. 321-336.
International Search Report PCT/KR2013/007595 dated Dec. 26, 2013.

* cited by examiner

Doxorubicin HCL 1 nm

CARBON NANOTUBE-BASED ANTI-CANCER AGENT CAPABLE OF SUPPRESSING DRUG RESISTANCE

CROSS-REFERENCE TO RELATED APPLICATIONS

This application is a 371 of PCT/KR2013/007595, filed Aug. 23, 2013, which claims the benefit of Korean Patent Application No. 10-2012-0092644, filed Aug. 23, 2012, the contents of each of which are incorporated herein by reference.

FIELD OF THE INVENTION

The present invention relates to nanotechnology-based anticancer agents, and provides a radical solution capable of relieving side effects of drugs mentioned as a big problem. More specifically, the present invention provides a technology which can regulate the degree of covalent bonding between a multi-walled carbon nanotube and anticancer compounds and maximize the effect of a small amount of drugs thereby.

BACKGROUND OF THE INVENTION

Although methods for treating cancer include a surgical treatment, a radiation therapy and a chemotherapy, these treatments are accompanied by side effects, or the treatment is limited to apply according to the degree of progression of cancer. In particular, anti-cancer drugs have been expanded in terms of quantity as results of repetitive researches, but there was no significant change in terms of quality. The reason for these results is that most anti-cancer drugs are applied to cells whose somatic division is vigorous, with a mechanism of stopping cell cycle and inducing apoptosis of cancer cells and this mechanism results in typical side effects such as chemotherapy alopecia, anorexia, and lowered immunity due to leucopenia since the anticancer drugs attack normally dividing cells.

To minimize the side effects of anticancer drugs, targeted cancer drugs have been developed. Up to date, 18 or more of the targeted anticancer drugs have been developed and clinically applied, and more than 200 clinical trials are under investigated. However, these targeted anticancer drugs targeting a specific target have a limit that it may have effect to a cancer expressing the specific target among same type of cancers have a problem that the cancer gets resistance to the targeted anticancer drugs since it should be administrated over a long period of time. In order to compensate this problem, a cocktail therapy combined with prior potent anticancer drugs or a method using a single anticancer drug which attacks multiple targets simultaneously has been used. However, these methods imply risk of causing serious side effects.

Carbon nanotubes have been used in various biomedical fields including imaging and cancer therapy due to their mechanical, optical and chemical properties (Liu, Z. et al., *Nano Res.*, 2:85, 2009; De La Zerda, A. et al., *Nat. Nanotechnol.*, 3(9): 557-62, 2008; Cherukuri, P. et al, *J. Am. Chem. Soc.*, 126(48): 15638-9, 2004; Welsher, K. et al., *Nano Lett.*, 8(2): 586-90, 2008; Zavaleta, C. et al., *Nano Lett.*, 8(9): 2800-5, 2008). Carbon nanotubes as drug delivery materials undergo endocytosis and have been investigated as in vitro drug delivery systems for delivering various biomolecules including anticancer drugs (Liu, Z. et al., *ACS Nano.*, 1(1): 50-6, 2007; Bianco, A. et al., *Curr. Opin. Chem. Biol.*, 9(6): 674-9, 2005), plasmid DNA (Liu, Y. et al., *Angew. Chem. Int. Ed.*, 44: 4782, 2005), and siRNA (small interfering RNA) (Kam, N. W. et al., *J. Am. Chem. Soc.*, 127(36):12492-3, 2005) to cells effectively. Most of previous researches on drug delivery system using carbon nanotubes have been focused to a method for delivering anticancer drugs using single-wall carbon nanotubes to cells. The previous researches used methods for loading anticancer drugs to the single-wall carbon nanotubes using π-π (pi-pi) stacking after coating PEG (polyethylene glycol) on the surface of the single-wall carbon nanotubes (Liu, Y. et al, *Angew. Chem. Int. Ed.*, 48:7668-7672, 2009; Liu, Z. et al, *ACS. NANO*, 1(1): 50-56, 2007; Liu et al, *J. Am. Chem. Soc.*, 129, 8438-8439, 2007).

DETAILED DESCRIPTION OF THE INVENTION

Technical Problems

The factor that has been recognized as an important factor in the field of anticancer agents using carbon nanotubes is increasing the ratio of anticancer drug loaded onto a carbon nanotube to carbon nanotube. For this reason, π-π bond based on hydrophobicity has been used, but this approach has a disadvantage that the anticancer drugs are released so rapidly from the carbon nanotubes. Although this may be interpreted to be provided in order to maximize the efficacy of anticancer drugs, anticancer drugs bonded with carbon nanotubes by π-π bonds may not show a more excellent antitumor activity than conventional anticancer drugs to which a nanotechnology is not applied when the carbon nanotube-based anticancer drugs are treated to a cancer resistant to anticancer drugs since they may be pumped out from cancer cells rapidly due to the change of pH and this may result in pumping out of the anticancer drugs from the cancer cells before the cancer cells are proliferated and divided (mainly 12 to 48 hours) thereby.

In addition, when carbon nanotube-based anticancer drugs are administrated in vivo, they tend to circulate very fast and be accumulated in particular organs and circulate within blood vessel for a long time depending on their surface properties. Therefore, it is possible to cause accumulation of carbon nanotubes in organs, hepatotoxicity, toxicities due to hematic reaction and perturbation of immune system thereby.

Thus, the present invention is provided to solve the above-mentioned problems, including side effects of carbon nanotube-based anticancer drugs based and resistance to anticancer drugs, particularly, an anticancer drug based on carbon nanotube capable of providing an excellent cancer cell death activity despite a very small amount of anticancer drugs are loaded to carbon nanotubes and a method for treating cancer using the same. The anticancer drug according to the present invention may be effective clinically by removing side-effects of conventional anticancer drugs due to using very small amount of anticancer drugs as well as be effective to cancers resistant to conventional anticancer drugs. However this purpose is illustrative, thus the scope of the present invention is not limited thereto.

SUMMARY OF THE INVENTION

In an aspect of the present invention, an anticancer agent comprising a multi-walled carbon nanotube, and anticancer drug attached covalently thereto is provided.

According the anticancer agent, the multi-walled carbon nanotube may have a diameter of 5 to 50 nm, and the length thereof may be from 100 to 350 nm.

Further, the multi-walled carbon nanotubes may have a surface modified with a carboxyl group, the surface of the multi-walled carbon nanotubes may be modified to have 10 to 35% carboxyl groups. The content of the carboxyl group covalently is a very important factor since it is proportional to the content of covalent bonds between drugs and the carbon nanotubes and thus in case that the surface of the carbon nanotubes has less than 10% of carboxyl group the amount of available drugs would be very low. Moreover, although the content of the carboxyl group may be more than 35% of the surface of carbon nanotubes, the anticancer drug of the present invention capable of releasing drugs in long term and continuously does not need to use large amount of drugs.

In addition, the anticancer drug may be bonded to a multi-walled carbon nanotube modified with EDC (N-(3-Dimethylaminopropyl)-N-ethylcarbodiimide hydrochloride) linker under the condition of pH 5.9~6.2, wherein the multi-walled carbon nanotube modified with EDC linker is made by reacting the EDC linker and the multi-walled carbon nanotube under the condition of pH 5.2~5.5. Through the process, drug loading capacity of carbon nanotube was improved twice to the conventional covalently bonded carbon nanotube-based anticancer drug and even the anti-cancer agent of the present invention has deformed structure.

The anticancer drug may be covalently bonded to the surface of carboxylated multi-walled carbon nanotubes by EDC linker.

In addition, the anticancer drug may be an amine-based compound, such as doxorubicin, epirubicin, adriamycin, cis-platin, mitomycin-C and daunomycin, etc.

The anticancer drug may be loaded at a ratio of 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, or 35 wt % to the multi-walled carbon nanotube, preferably 23 to 35 wt %, more preferably 23-30 wt % of anticancer drug may be loaded to the multi-walled carbon nanotubes, and the degree of loaded anticancer drug is dependent on the content of the carboxyl groups, the mode of drug attachment according to pH adjustment. The present inventors confirmed that anti-cancer drug-carbon nanotube complexes which are covalently conjugated by an embodiment of the present invention manufactured had very low dissociation rate of the anticancer drug from the carbon nanotube by being attached strongly to the carbon nanotubes even that entire structure was deformed according to increasing of the amount of anticancer drugs covalently bonded to the carbon nanotubes (See FIGS. 11 to 13). In other words, the anticancer agent according to an embodiment of the present invention has increased loading ratio of anticancer drug compared to conventional carbon nanotube-based anticancer agent and this increased loading ratio results in the enforcement of binding between the carbon nanotube and the anticancer drug. This means that the dissociation rate between the anticancer drugs and the carbon nanotubes in cancer cells and it is possible to maximize anticancer effect to cancer cells including cancer cells resistant to anticancer drugs by releasing anticancer drugs very slowly due to decreased dissociation rate between the anticancer drugs and the carbon nanotubes within cancer cells.

The anticancer drug may include epidermal growth factor (EGF). EGF receptors are known to be overexpressed in lung cancer cells, thus the anticancer agent including the EGF may target to cancer tissue.

The anticancer agent of the present invention may be used for treating a cancer selected from the group consisting of liver cancer, colon cancer, cervical cancer, renal cancer, gastric cancer, prostate cancer, breast cancer, brain cancer, lung cancer, cervical cancer, colon cancer, bladder cancer, blood cancer and pancreatic cancer. The anticancer agent may be more effective for treating liver cancer or lung cancer, considering that the multi-walled carbon nanotubes are accumulated mainly in liver and lung.

In another aspect of the present invention, a pharmaceutical composition for treating cancer comprising: (a) a pharmaceutically effective amount of the anticancer agent according to an embodiment of the present invention and (b) a pharmaceutically acceptable carrier is provided.

The pharmaceutical composition is preferably administered parenterally and the case of parenteral administration, intravenous injection, subcutaneous injection, intramuscular injection, and intraperitoneal injection, etc. may be used.

The suitable dose of the pharmaceutical composition may be varied by various factors such as mode of administration, age, body weight, sex, pathologic condition, food, administration time, administration route, excretion rate and reaction sensitivity and a skilled physician may determine and prescribe dose effective for desired treatment and prevention easily. According to a preferred embodiment of the invention, a suitable daily dose may be 100 µg/kg to 1 mg/kg (body weight). The pharmaceutical composition of the present invention may be administered once a day, as divided several times for several weeks.

Further, according to an embodiment of the invention the pharmaceutical composition of the present invention may be formulated by preparing in a unit dosage by formulating using a pharmaceutically acceptable carrier and/or excipient or prepared as enclosed in a multi-dose container. In this case, the formulation may be a solution, suspension or emulsion form or extracts, powders, granules, tablets or capsules and a dispersant or a stabilizer may be additionally included thereto.

Further, the pharmaceutical composition according to an embodiment of the present invention may be administrated at a dose of 100 µg/kg to 1 mg/kg which is very small amount compared with dosage of conventional anticancer drugs, 5~30 mg/kg. The dose may be adjusted depending on age, sex, pathological condition of patients.

In another aspect of the present invention, a method of treating cancer comprising administrating an anticancer agent comprising a multi-walled carbon nanotube, and anti-cancer drugs covalently bonded to the multi-walled carbon nanotube to a subject suffering cancer is provided.

According to the method of treating cancer, the cancer may be liver cancer, colon cancer, cervical cancer, renal cancer, gastric cancer, prostate cancer, breast cancer, brain cancer, lung cancer, cervical cancer, colon cancer, bladder cancer, blood cancer or pancreatic cancer.

The subject suffering cancer may be a human or a non-human mammal.

In addition, the anti-cancer drug may be an amine-based compound and the anticancer drug may be doxorubicin, epirubicin, adriamycin, cis-platin, mitomycin-C and daunomycin, etc.

In another aspect of the present invention, a drug delivery composition for delivery a drug to liver of lung comprising a multi-walled carbon nanotubes, and the drug covalently coupled to the carbon nanotube is provided.

The drug delivery composition for delivering a drug to liver or lung may be prepared by modifying the multi-walled carbon nanotube as having carboxyl groups, and the drug may be loaded at a ratio of 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, 30 wt %, 31 wt %, 32 wt %, 33 wt %, 34 wt %, or 35 wt % to the multi-walled carbon nanotube, preferably 23 to 35 wt %, more preferably 23-30 wt % of drug may be loaded to the multi-walled carbon nanotubes. In addition, the drug may be bonded to a multi-walled carbon nanotube modified with EDC (N-(3-Dimethylaminopropyl)-N-ethylcarbodiimide hydrochloride) linker under the condition of pH 5.9~6.2, wherein the multi-walled carbon nanotube modified with EDC linker is made by reacting the EDC linker and the multi-walled carbon nanotube under the condition of pH 5.2~5.5. The drug may be an anime-based compound.

The present inventors found that the drug delivery composition was distributed to liver and lung tissue when it is administrated in vivo. This property shows that the drug delivery system of the present invention may be used for delivering various drugs beside anticancer drugs to liver and/or lung tissue effectively and treating and/or preventing liver disease or pulmonary disease thereby. Particularly, the drug delivery system of the present invention may be used for treating chronic diseases without side effects by releasing the drugs slowly at the pathogenic site since the dissociation rate of the drugs at the pathogenic site is low. The liver disease may be selected from the group consisting of cirrhosis, hepatitis, alcoholic liver disease, fatty liver, liver hemangioma, primary biliary cirrhosis, primary sclerosing cholangitis, Bud-Chiari syndrome and hemochromatosis, and the pulmonary disease may be selected from the group of consisting of asthma, emphysema, chronic obstructive pulmonary emphysema, centrilobular emphysema, panacinar pulmonary emphysema, lung fibrosis, pneumoconiosis, pulmonary congestion, atelectasis, and interstitial lung disease. In addition, the interstitial lung disease may be sarcoidosis, idiopathic pulmonary fibrosis (IPF), nonspecific interstitial pneumonia (NSIP), cryptogenic organizing pneumonia (COP), desquamative interstitial pneumonitis (DIP), respiratory bronchiolitis-interstitial pneumonia (RBILD), acute lung enteritis (AIP), lymphangioleiomyomatosis (LAM), pulmonary Langerhans's cell histiocytosis (PLCH) or eosinophilic pneumonia, etc.

Advantageous Effect of the Invention

As described above, according to one embodiment of the present invention, carbon nanotube-based anticancer agent with high anticancer effect and low toxicity may be achieved. Of course, this effect of the present invention does not limit the scope of the present invention.

BEST MODES FOR THE INVENTION

Figure 1:
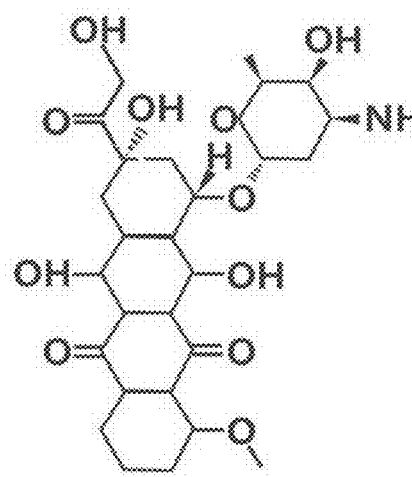
FIG. 1 is a transmission electron microscopic image showing carboxylated surface of MWNTs (right), and a schematic diagram showing a virtual appearance of a covalent bonding of doxorubicin to carboxyl group of a carboxylated multi-walled carbon nanotube (left).
Figure 1:
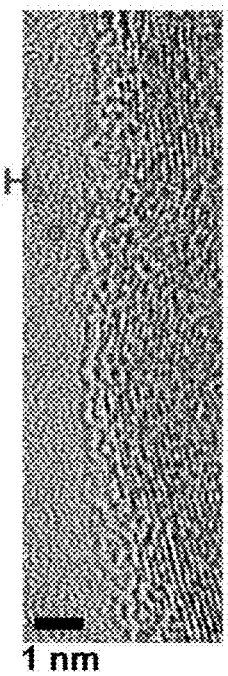

The terms used in this document are defined as follows:

An "effective amount" used in this document means an amount sufficient to exert therapeutic effect.

A "pharmaceutically acceptable carrier" used in this document means a material used to prepare a formulation, and includes: a carbohydrate-type compound (for example, lactose, amylose, dextrose, sucrose, sorbitol, mannitol, starch, cellulose, etc.), gum acacia, calcium phosphate, alginates, gelatin, calcium silicate, microcrystalline cellulose, polyvinylpyrrolidone, cellulose, water, syrup, salt solutions, alcohols, gum Arabic, vegetable oils (such as corn oil, cotton seed oil, soy oil, olive oil, coconut oil), polyethylene glycol, methyl cellulose, methyl hydroxybenzoate, propyl hydroxybenzoate, talc, magnesium stearate and mineral oils, but are not limited thereto. The pharmaceutical composition of the present invention may further comprise a lubricant, a humectant, a sweetener, a flavoring agent, an emulsifier, a suspending agent, a preservative, etc. Suitable pharmaceutically acceptable carriers and formulations are described in detail in Remington's Pharmaceutical Sciences (19$^{th}$ ed., 1995), which is incorporated herein by reference.

The present invention will be described more specifically as follows:

The present invention is directed to an anticancer compound comprising a multi-walled carbon nanotube and anticancer drugs covalently attached thereto.

The anticancer compound according to an embodiment of the present invention provides an effect of slow release of anticancer drugs from the multi-walled carbon nanotube over several times for a period of time.

Previously, anticancer drugs have been attached to carbon nanotubes using pi-pi ($\pi$-$\pi$) bond. Although this bond has extremely higher capacity than covalent bond (the loading rate of $\pi$-$\pi$ bond is about 200%, the loading rate of covalent bond is about 4~16%, wherein the loading rate refers to mass of cancer drug loaded to a carbon nanotube compared with average mass of carbon nanotubes), it's one of features is that the anticancer drugs are released from carbon nanotubes rapidly. Most researchers have considered increased loading rate as a benefit of carbon nanotube-based anticancer drugs and have expected that these carbon nanotube-based anticancer drugs would be very effective to treat cancer. However, since a large amount of anticancer drugs are released from cancer cells before the cells proliferate, these carbon nanotube-based anticancer drugs are neither significantly superior to single chemotherapeutics which are not based on nanotechnology nor provide clues capable of solving toxicity problem of carbon nanotubes and anticancer drugs. The reason is that this approach did not prove therapeutic effect of very small amount of anticancer drugs which can suppress the side effects.

Further, the conventional carbon nanotube-based anticancer drugs using pi-pi bond have not provided alternatives to drug resistance. Efflux of anticancer drugs from cancer cells due to drug resistance which has been recognized in recent studies is a process whereby cancer cells expel anticancer drugs to the outside of cells through pumping by drug resistant gene products expressed in cancer cells after uptaking the anticancer drugs, and it has been known that as cells are more resistant to drugs the cells' ability to pump the drugs gets stronger. For this reason, when treating cancer patients who have drug resistance, there is problem that dose of drugs should be increased continuously. In this case, toxicity of the drug itself such as hepatotoxicity, cardiotoxicity, and myelosuppression is increased and this makes chemotherapy procedure a very painful one.

The present inventors hypothesized that an anticancer agent made by strongly attaching anticancer drugs to carbon nanotubes through covalent bond may be more effective than conventional anticancer drugs and be an alternative to solve drug resistance on the contrary to the conventional concept. Although the amount of anticancer drugs loaded to carbon nanotube is very small compared to that prepared by pi-pi bond, the feature that anticancer drugs are released slowly within cancer cells is expected to maximize therapeutic effect of anticancer drugs even by administrating very small amount of anticancer drug compared with conventional anticancer drugs and to elevate apoptotic effect of anticancer drugs thereby, since it can solve the problem of rapid efflux of anticancer drugs by drug-resistant cancer cells. To verify the hypothesis, the present inventors prepared an anticancer agent comprising multi-walled carbon nanotubes and anticancer drugs covalently attached thereto and confirmed in vitro and in vivo therapeutic effect of the anticancer agent and evaluated stability of the anticancer agent to which anticancer drugs loaded. As results, an anticancer agent prepared by covalent attachment of small amount of anticancer drugs to multi-walled carbon nanotubes had more significant anticancer therapeutic effect than simple anticancer drugs when treated to cancer cells or administrated to tumor model animals. This mechanism of treatment is basically that anticancer drugs are released from the carbon nanotubes continuously in cancer cells due to strong covalent bond between the anticancer drugs and the carbon nanotubes. The degree of bond between the anticancer drugs and carbon nanotubes was significantly increased according to increasing loading rate of the anticancer drugs by elevating the degree of carboxylation of the carbon nanotubes and adjusting pH in two steps in the preparing procedure.

Taken together, the result of the present invention that the carbon nanotube-based anticancer agent according to an embodiment of the present invention has excellent anticancer effect compared to conventional anticancer drugs even though a very small amount is used was reported at the first time. This result suggests that the carbon nanotube-based anticancer agent according to an embodiment of the present invention may be applied as a new approach to treat cancer and solve drug resistance problem.

Modes for the Invention

Hereinafter, Examples and Experimental Examples of the present invention will be described in further detail below. However, the invention is not limited to the Examples and Experimental Examples described below and may be implemented as different forms and the following Examples and Experimental Examples of the present invention are provided in to fully disclose the invention and inform the ordinary skilled the scope of the invention.

EXAMPLE 1

Preparation of Carbon Nanotube-based Anticancer Agents 1-1: Preparation of Carboxylated Multi-walled Carbon Nanotubes (mwCNT-COOH)

Since nanotubes tend to aggregate easily due to van der Waals attraction, it is difficult to suspend the nanotubes in solvent. Thus, the present inventors used acid in order to oxidize the carbon atom of the ends and defected regions of carbon nanotubes. By oxidizing the surface of the carbon nanotubes using acidic solvents, functional groups such as carboxylic group may be introduced. The present inventors prepared surface-functionalized carbon nanotubes in which carboxylic groups are introduced as follows:

The process for introducing carboxylic group was carried out by applying functional groups including oxygen to the surface of carbon nanotubes by suspending the carbon nanotubes in strong acidic solvent (a); and sonicating the acidic solvent comprising the carbon nanotubes (b). Twenty mg of multi-walled carbon nanotubes (mwCNTs) having diameter of 10-30 nm (Lot No: NT-0149, Catalog No. 900-1351, SES Research Inc.) were preheated at 300° C. in order to remove vapor and contaminants and treated with added to a mixture of 9 ml of 98% $H_2SO_4$ and 3 ml of 65% $HNO_3$ (volume ratio: 3:1). Next, the solution was sonicated again for 15 min and filtered by mesh (100 μm), diluted with deionized (DI) water (1:200 v/v), and filtered (200 nm pore size PTFE, Millipore) with wash out several times to remove any residual solvent. The resultant mwCNTs were then dried in a vacuum oven at.

And then, the present inventors scraped the functionalized mwCNTs from the filter paper by medicine scrape (stainless steel). This treatment provides carboxylic acid groups (—COOH) at defects on the surface of carbon nanotubes. The carboxylation of defects of carbon nanotubes enhances solubility of the carbon nanotubes in water or organic solvents.

1-2: Preparation of mwCNTs to which EDC Linker is Attached (EDC-mwCNT-COOH)

EDC is a zero-length cross-linker widely used in protein conjugations. The conjugation reactions occur in two sequential steps. The EDC first reacts with a carboxyl group, forming an amine-reactive O-acylisourea intermediate to reacts with an amine group for producing a stable amide bond. However, the O-acylisourea intermediate is very unstable and susceptible to hydrolysis. Such instability results in low coupling efficiency. The addition of NHS (N-hydroxysuccinimide or its more water soluble analogue Sulfo-NHS) stabilizes the intermediate by converting it to a semistable amine-reactive NHS ester, thus increasing the coupling efficiency by 10-20 fold.

The coupling is typically performed at slightly acidic pH in MES buffer (2-morpholino-ethanesulfonic acid). MES buffer (low moisture content ≥99%, Sigma-Aldrich, CAT: M3671) was used for adjusting pH of the solution. Firstly, 3.2 mg of mwCNT-COOH was dispersed in 1.6 ml of MES buffer (50 mM, pH 5.5) by tip sonicator (Misonix sonicators, Product: Sonicator 4000) with frequency of 3 s on/3 s off for 5 min. Secondly, 400 mM NHS (N-hydroxysuccinimide, Sigma) solution in MES buffer (50 mM, pH 5.5) was added to the mwCNT-COOH solution and vortexed for 30 min. And then, EDC (1-ethyl-3-(dimethyl-aminopropyl)carbodiimide hydrochloride, 300 mM, Sigma) dissolved in MES buffer solution was added to the reacted functionalized mwCNT solution and the mixture was stirred for 30 min. The mixture solution was then dispensed into filter tubes (Amicon YM-50, Millipore), centrifuged at 3000 rpm for 10 min, and rinsed with 50 mM MES buffer at least three times, and thus carbon nanotubes linked with EDC linkers (EDC-mwCNTs) were prepared.

1-3: Preparation of Carbon Nanotube-based Anticancer Agents

The carbon nanotube-based anticancer agent according to an embodiment of the present invention has higher rate of attachment of anticancer drugs than previous anticancer drugs using covalent bond. In order to enhance the rate of attachment rate of anticancer drugs, the present inventors adjusted pH values in the EDC linker attaching step and drug attaching step, respectively. The present inventors chosen pH 5.5 among range of pH 4-6 which is an optimal condition for attaching EDC linkers and elevated pH to 6.1 in the drug attaching step. Although pH 6.1 does not meet the optimum condition for attaching drugs, it can inhibit hydrolysis of EDC linkers. Thus, the change of pH in two phases (pH 5.5 and 6.1) can maximize loading rate of anticancer drugs as well as maintain bonds by EDC linkers stably thus induce strong covalent bond between CNTs and drugs.

Particularly, the present inventors carried out following experiments in order to increase loading rate of drugs as well as maintaining bonds by EDC linkers as described above. The EDC-mwCNT solution prepared in the Example 1-2 was mixed with anticancer agents, doxorubicin (Sigma-Aldrich, Cat# D1515) or epirubicin hydrochloride (EPI, Sigma-Aldrich, Cat# 9406), respectively. Drugs and CNTs with ratios of 1:4, 1:2 and 1:1, respectively were mixed and pH was adjusted to 6.1 and the mixture was agitated using a platform shaker for at least 24 hour at 4° C. After the agitation, solution of EDC-mwCNT bound to drugs was centrifuged in Amicon YM-50 filter tubes at 3000 rpm for more than 3 times, to remove unconjugated drugs. Last, drug-loaded mwCNTs (DOX-mwCNTs and EPI-mwCNTs) were dispersed in 5 ml of PBS and used for the following experiments.

1-4: Preparation of mwCNTs onto which Drugs and EGF are Loaded

The EDC-mwCNT solution prepared in the Example 1-2 was mixed with EGF (Sigma, E9644) and doxorubicin (DOX) or epirubicin hydrochloride (EPI). At this time, the mixing ratio of EDC-mwCNT:drugs (doxorubicin or epirubicin):EGF was 5:5:1. Thereafter, the mixture was agitated using a platform shaker for 14-18 hours at 4° C. After the agitation, solution of EDC-mwCNT onto which drugs and EGF are loaded was centrifuged in Amicon YM-50 filter tubes at 2000 rpm, to remove unconjugated drugs. An then, the mwCNT onto drugs and EGF are loaded (mwCNT (Dox-EGF-mwCNT, EPI-EGF-mwCNT) was is dissolved in 5 ml of PBS.

1-5: Composition of the Combination Drug and the Production of EGF

Doxorubicin linked with EGF (DOX-EGF) or epirubicin linked with EGF (EPI-EGF) were prepared by the method described in the above Example 1-4 as drug (doxorubicin or epirubicin): EGF mixing ratio was 5:1, respectively.

TABLE 1

Carbon nanotube-based anticancer agent of an embodiment of the present invention

| | Designation | Abbreviations |
|---|---|---|
| Multi-walled carbon nanotubes | Multi-walled carbon nanotube | mwCNT |
| Doxorubicin | doxorubicin | DOX |
| Epirubicin | epirubicin | EPI |
| Carboxylated carbon nanotubes | mwCNT-COOH | mwCNT-COOH |
| Carboxylated carbon nanotubes + EDC linker | EDC-mwCNT-COOH | EDC-mwCNT |
| Carboxylated carbon nanotubes + anticancer drug | DOX-mwCNT-COOH EPI-mwCNT-COOH | DOX-mwCNT EPI-mwCNT |
| Carboxylated carbon nanotubes + EGF + anticancer drug | DOX-EGF-mwCNT EPI-EGF-mwCNT | DOX-EGF-mwCNT EPI-EGF-mwCNT |
| EGF + anticancer drug | | DOX-EGF EPI-EGF |

EXAMPLE 2

Preparation of Animal Models of Tumor

Females (n=15) BALB/c nude mice (20 g, Gyeongsang National University School of Medicine Laboratory Animal Room) was raised under the condition of controlled temperature, free feeding and light cycle of 6:00 to 18:00.

To prepare the animal tumor model, MDA-MB-231 cells were inoculated subcutaneously in the flank of female BALB/c nu/nu (athymic nude) mice ($5 \times 10^6$ cells per mouse) When the tumor reached a mean volume of 100 mm$^3$ in the mice were used for the following Experimental Examples.

EXPERIMENTAL EXAMPLE 1

Identification of Characteristics of Carbon Nanotube-based Anticancer Agents 1-1: Visualization of Carbon Nanotubes and Carbon Nanotube-based Anticancer Agents The inventors took images of the mwCNTs-COOH prepared in the above Example 1-1 in order to visualize carboxylic group of the mwCNTs-COOH with a high-resolution transmission electron microscope (FE-TEM, JEM 2100F, Japan) operating with 200 kV (FIG. 1). As a result, as shown in FIG. 1, the outer surface of mwCNTs was not smooth rather rugged. As a result of measuring the size of mwCNTs based on the transmission electron microscopic images, the diameter of the mwCNTs-COOH was measured of about 30-50 nm. All mwCNT samples were subjected to TEM imaging after diluting with ethanol and sonicating for 2 min.

Figure 2:
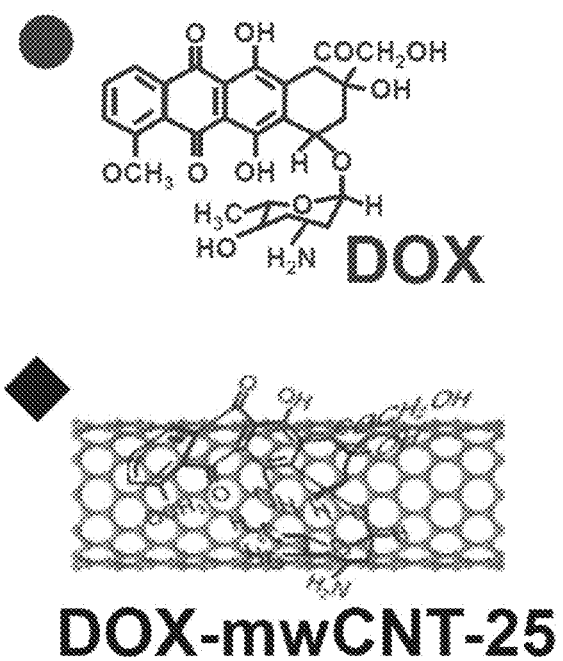
FIG. 2 is the structural formula of doxorubicin (top) and a form of complex to which a carbon nanotube is covalently bonded (bottom).
Figure 3:
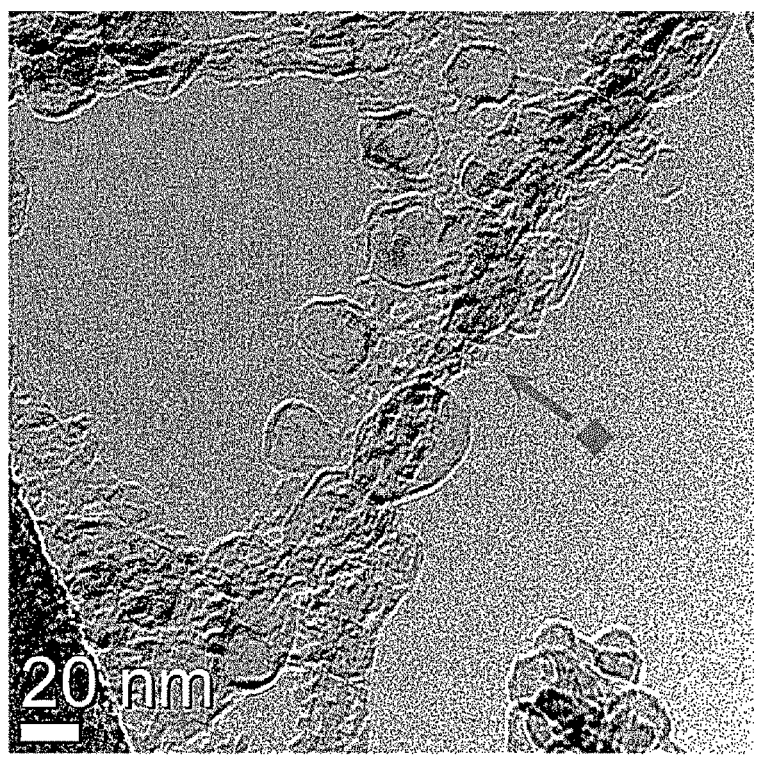
FIG. 3 is a transmission electron microscopic image of doxorubicin covalently bonded to a multi-walled carbon nanotube.
Figure 4:
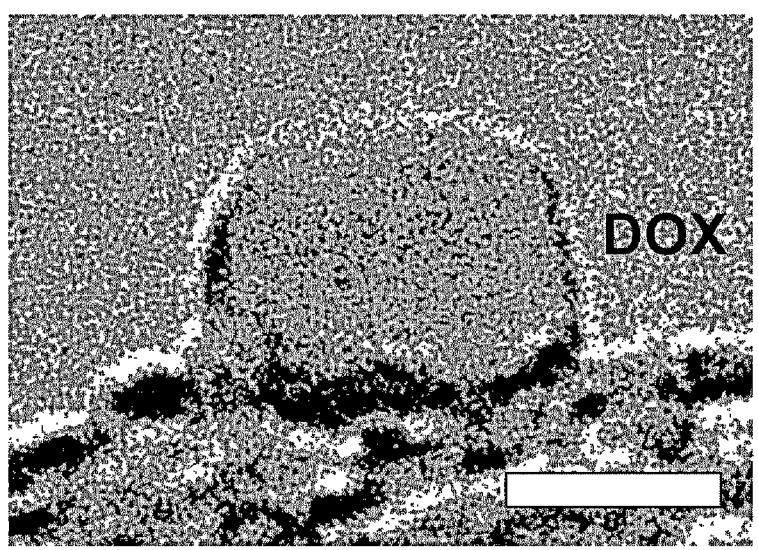
FIG. 4 is a magnified high-resolution transmission electron microscopic image of doxorubicin covalently bonded to a multi-walled carbon nanotube.

FIG. 2 is a schematic diagram representing appearance of doxorubicin attached to mwCNT. The present inventors took images of doxorubicin covalently linked to mwCNT using a freeze-transmission electron microscope (Cryo-TEM, F20, Tecnai) in order to visualize drugs covalently bonded to mwCNT (FIG. 3). As a result, as shown in FIG. 3, images of doxorubicin covalently linked to carbon nanotube were successfully taken at the first time. Furthermore, the present inventors took images using a high-resolution transmission electron microscope (FE-TEM, JEM 2100F, Japan) in order to visualize more accurate images of doxorubicin (FIG. 4). As a result, as shown in FIG. 4, the shape of doxorubicin was oval.

Figure 5:
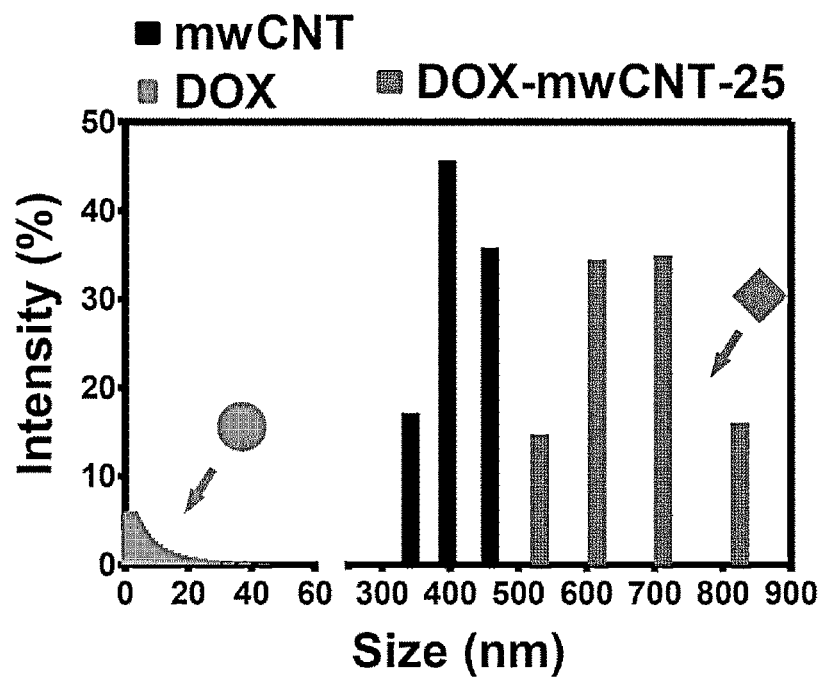
FIG. 5 is a graph showing the distribution of particle size of doxorubicin, carboxylated MWNTs and carboxylated MWNTs covalently bonded to doxorubicin (DOX-mwCNT-25), respectively.

Particle sizes of DOX, oxidized mwCNT-COOH, and DOX-mwCNT-25 measured using transmission electron microscope showed length variation of 0-40, 350 450, and 500-830nm, respectively (FIG. 5), and exhibited polydispersity ranging between 0.1 and 0.5, depending on the prepared sample densities in PBS.

1-2: Confirmation of the Carboxylation of Carbon Nanotubes Through FT-IR Analysis Fourier transform infrared spectroscopy (FTIR, VERTEX 80v, Bruker Optics) was performed to analyze carboxyl formation on mwCNTs.

Figure 6:
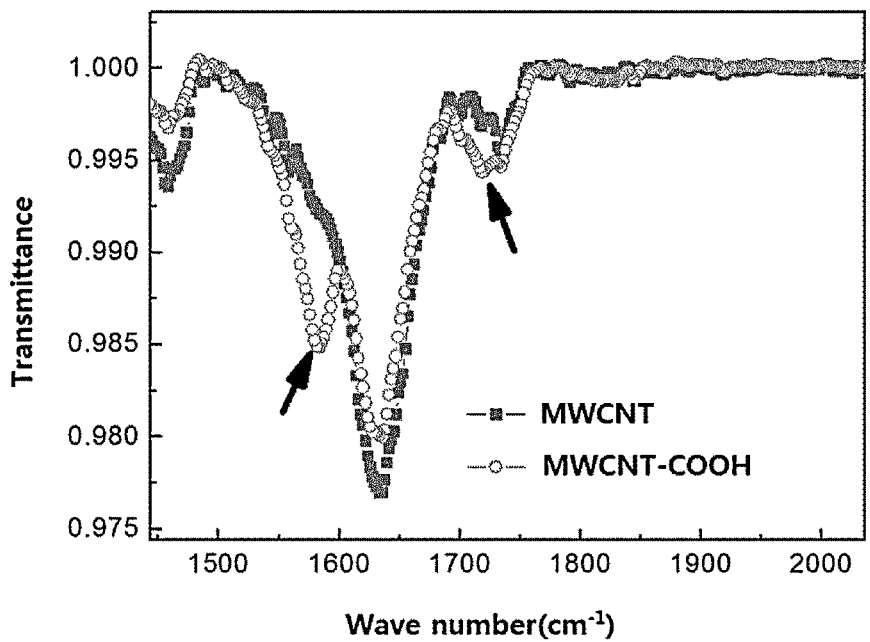
FIGS. 6 and 7 are graphs representing results of successful carboxylation of multi-walled carbon nanotubes using FT-IR and TGA assays, respectively.

As a result, as shown in FIG. 6, the spectrum of carboxylated mwCNT showed a peak in the infrared frequencies, particularly peaks corresponding to —CC=O— bond and —C=O— bond were observed in the vicinity of 1580 and 1710 $cm^{-1}$, respectively. In this result, it was proved that carboxylic groups were attached to the surface of mwCNTs successfully. On the contrary, the spectrum of non-carboxylated mwCNT showed very low absorption of infrared ray and this suggests that there is neither —C—C=O— bond nor —C=O— bond (See FIG. 6).

1-3: Confirmation of the Carboxylation of Carbon Nanotubes Through TGA Analysis

Thermal gravimetric analysis (TGA) was performed in order to confirm carboxylation of mwCNTs. Particularly, before the TGA analysis mwCNTs were heat-treated at 60° C. for 3 h in vacuum in order to evaporate residual water molecules from the surfaces. The TGA analysis was performed using Q50 TGA instrument (TA, USA) with increasing temperature at a rate of 10° C./min and under nitrogen flow at 100 mL/min.

Figure 7:
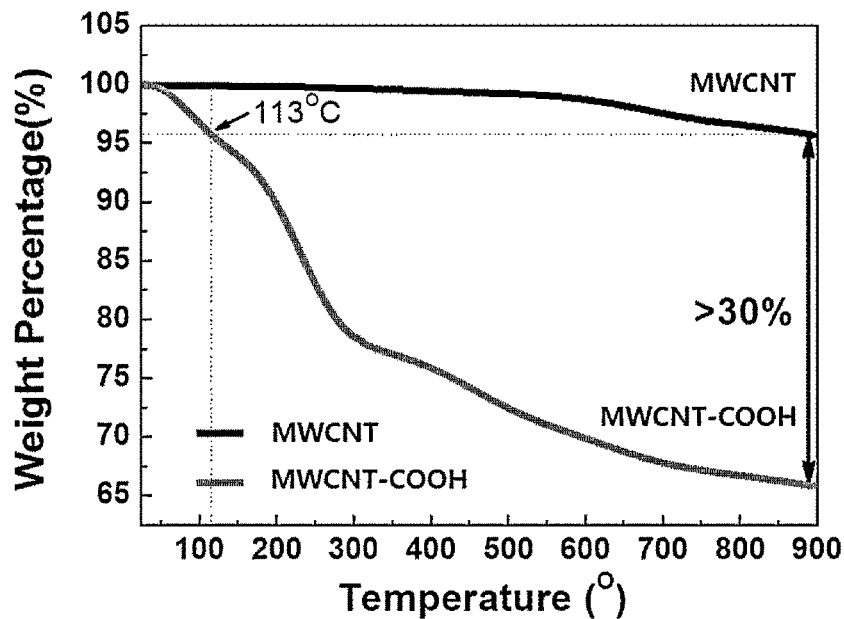

As a result, as shown in FIG. 7, it was confirmed that mwCNT-COOH showed about 35% of weight loss compared to non-carboxylated mwCNT. These results were ascertained to be due to loss of functional side chain of mwCNTs. Conversely, the degree of carboxylation of mwCNTs may correspond to the degree of weight lost (see FIG. 7).

1-4: Confirmation of Binding between Carbon Nanotubes and Anticancer Drugs

It was investigated whether anticancer drugs were normally linked to the carboxylated mwCNT prepared in the Example 1 through UV-vis (UV-Visible) absorption spectrum using a spectrometer (X-ma 3000 series, Human Corporation, South Korea).

Specifically, nano anticancer agents of the present invention dissolved in PBS was diluted about 10-30 times to measure the absorbance peak using a spectrophotometer (X-ma 3000 series, Human Corporation, South Korea) in order to measure amount of anticancer drugs loaded to the carbon nanotubes. As a control group for the drug-loaded mwCNT-COOH, mwCNT-COOH not loaded with drugs were used.

Figure 8:
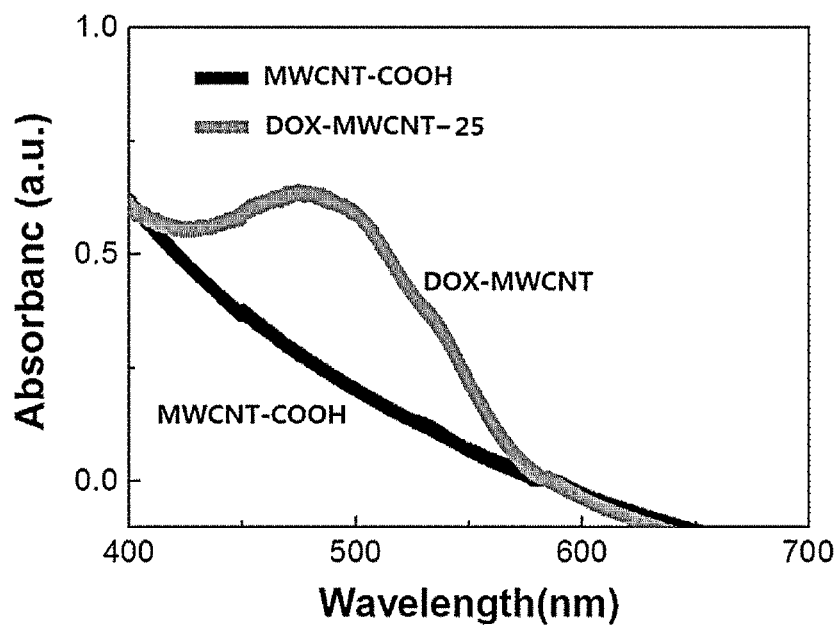
FIG. 8 is a graph showing the result of UV-vis analysis confirming that anticancer drugs, doxorubicin and epirubicin were covalently attached to carboxylated multi-walled carbon nanotube linked with EDC linkers (EDC-mwCNT-COOH).
Figure 9:
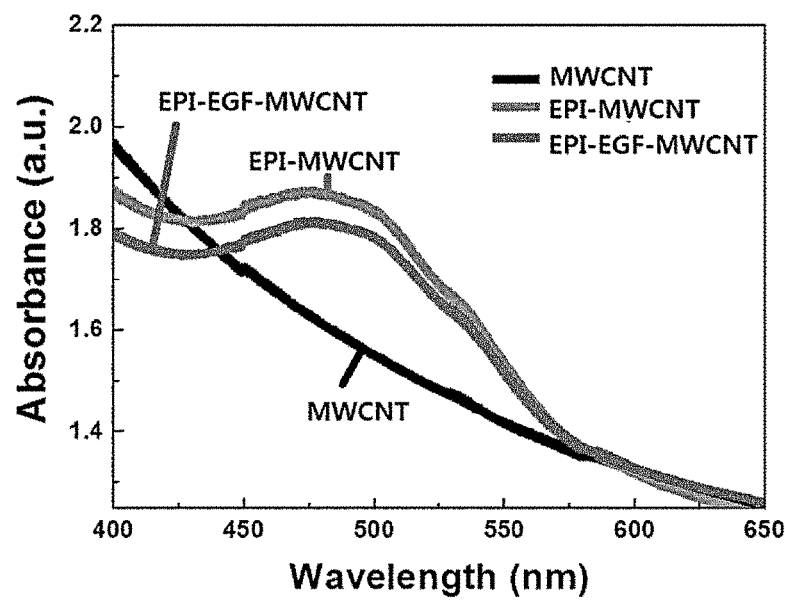
FIG. 9 is a graph representing the result of UV-vis analysis when epirubicin (EPI) is covalently attached to mwCNT-COOH and epirubicin and EGF are covalently attached to mwCNT-COOH.

As a result, as shown in FIGS. 8 and 9, the nano-anticancer drug that the drug is bound, such as doxorubicin and epirubicin, peaks were observed at about 490 nm. These results, I mean that the drug has been successfully attached to the carbon nanotube.

On the other hand, the mass ratio of the covalently bound doxorubicin or epirubicin on mwCNT is determined as the difference in absorption signal strength between the DOX-mwCNT or EPI-mwCNT, and the mass density in the solution was measured as standard curve of DOX and oxidized mwCNT.

Further, as shown in FIG. 9, EGF-EPI-mwCNT to which EGF is additionally attached showed decreased peak at the vicinity of about 490 nm and this suggests that a certain amount of EGF was attached to the carbon nanotubes along with drugs (see FIG. 9).

1-5: Measurement of Binding Strength between Anticancer Drug Doxorubicin and Carbon Nanotubes In order to analyze the degree of covalent bond between anticancer drugs and carbon nanotubes of the carbon nanotube-based anticancer agent according to an embodiment of the present invention, fluorescence of physically or non-specifically conjugated anticancer drugs and the carbon nanotube-based anticancer agents of the present invention was compared. In this case, the physically or non-specifically conjugated anticancer drugs mean refer to anticancer drugs prepared by mixing carbon nanotubes and anticancer drugs using simple pipetting, they were analyzed in comparison with the anticancer agents in which same amount of anticancer drugs and carbon nanotubes were covalently attached. In addition, pure doxorubicin was used as a control group in the whole experiments. To measure the degree of structural change of anticancer drugs attached to carbon nanotubes in comparison with the manner of binding and the strength of bond between the anticancer drugs and the carbon nanotubes, fluorescence emitted from doxorubicin was measured using a luminescence spectrometer (Perkin-Elmer, USA). Decrease of fluorescence of doxorubicin means that there was a structural change in the drug-carbon nanotube conjugate according to strong binding between doxorubicin and carbon nanotubes since doxorubicin itself is a fluorescent compound.

Figure 10:
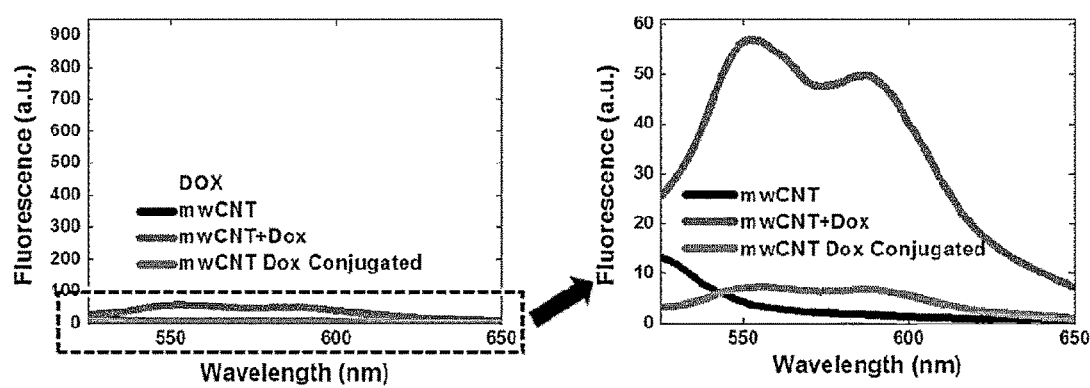
FIG. 10 is a graph representing the result of fluorescent analysis of the attachment of mwCNT and doxorubicin.

As a result, as shown in FIG. 10, doxorubicin, a single anti-cancer drug showed very high level of fluorescence, whereas carbon nanotubes, anticancer drug covalently bound to carbon nanotubes (DOX-mwCNTs, covalently conjugated) and anticancer drug physically bound to carbon nanotubes (DOX-mwCNT, physically conjugated) showed low fluorescence. Thus, upon comparing the intensity of the fluorescence of the above materials except pure doxorubicin, the intensity of the fluorescence of the anticancer drug covalently bound to carbon nanotubes was reduced about 88% in comparison with that of anticancer drug physically bound to carbon nanotubes.

When the intensity of the fluorescence of doxorubicin is determined as 100%, physically bound DOX-mwCNT showed about 6.3% of the fluorescence, covalently bound DOX-mwCNT showed about 0.8% of the fluorescence, thus it was confirmed that the fluorescence of covalently bound DOX-mwCNT was greatly reduced. In comparison, depending on methods of binding the intensity of these fluorescent, if the fluorescence intensity of physically bound DOX-mwCNT is determined as 100%, the fluorescence of covalently bound DOX-mwCNT is about 12%. These decreases in fluorescence intensity is due to structural changes of doxorubicin by interference and strong covalent bonds with carbon nanotubes, which proves that anticancer drugs are strongly linked to the carbon nanotube by covalent bond according to an embodiment of the present invention.

As a result of calculating the ratio of weight of covalently bound doxorubicin to that of carbon nanotubes (loading rate) in the doxorubicin-bound carbon nanotube prepared in the Example 1-3, the loading rate was 10%, 17% and 25-35% when weight ratios of 1:4, 1:2 and 1:1 were used, respectively. Thus, the present inventors designated doxorubicin-bound carbon nanotube prepared with a weight ratio of 1:1 as DOX-mwCNT-25 and used it mainly in the subsequent experiments.

Figure 11:
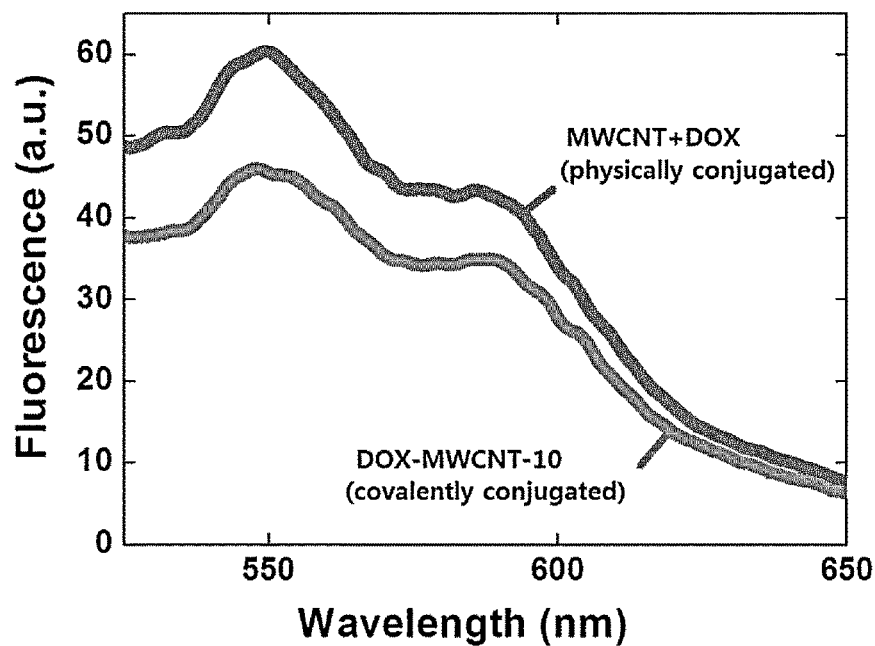
FIGS. 11 to 13 are graphs representing the change of fluorescent pattern depending on drug loading ratios of the carbon nanotube-based anticancer agent in accordance with an embodiment of the present invention.
Figure 12:
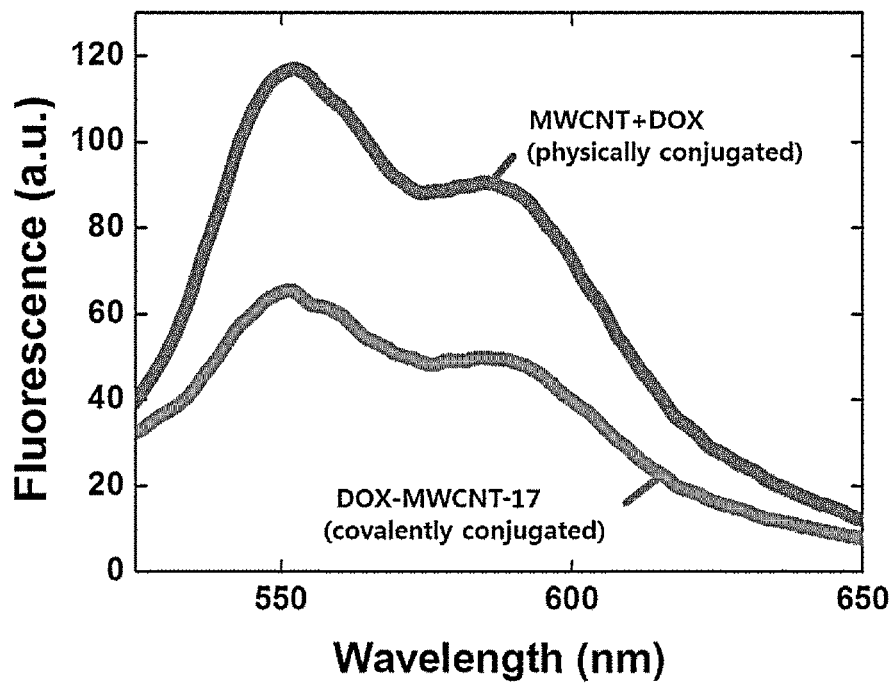
Figure 13:
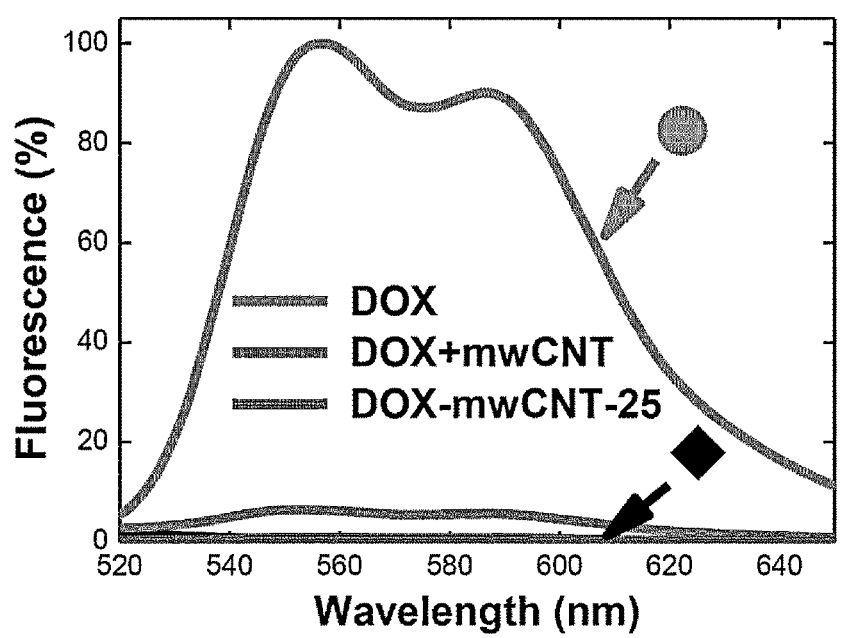

Analysis of the fluorescence of carbon nanotubes onto which doxorubicin with 3 different weight ratios were linked covalently revealed that there is a greater difference between the fluorescence intensities as the amount of drugs covalently bound to carbon nanotubes is increased, as shown in FIGS. 11-13.

EXPERIMENTAL EXAMPLE 2

Identification of Effect of the Carbon Nanotube-based Anticancer Agent Through In Vivo Experiments In order to confirm therapeutic effect of carbon nanotube-based anticancer agent according to an embodiment of the present invention, the change of tumor size (FIG. 15), weight (FIG. 16) and shape (FIG. 17) of tumors, the animal's body weight (FIG. 18) and tumor tissue (FIG. 19) were observed after administrating the carbon nanotube-based anticancer agent to BALB/c nude tumor model mice.

2-1: Changes in Weight and Size of Tumor

First, the tumor model mice prepared by transplanting MDA-MB-231 tumor cells to BALB/c nude mice were randomly divided into seven groups (n=10 per group) and injected with 200 μL of 0.5 mg/kg DOX, mwCNT, DOX-mwCNT in PBS, or pure PBS (negative control) in the tail vein. Subjects were weighed at 2, 9, and 16 days. Body weight and tumor sizes were measured twice a week for 21 days, and tumor volumes were calculated by the formula:

$$V(\text{volume})=X(\text{length}) \times D(\text{width})^2/2.$$

Figure 14:
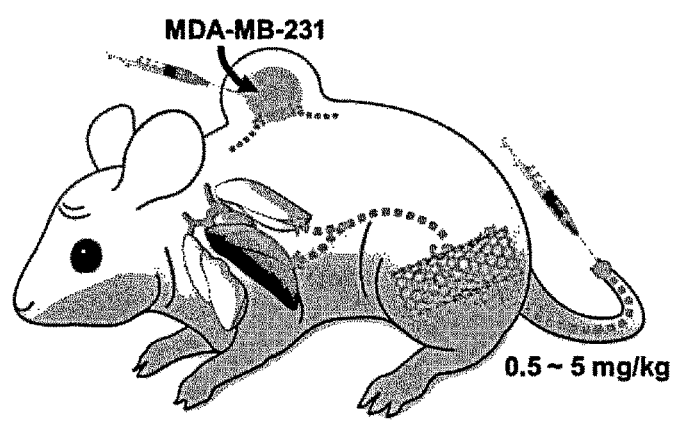
FIG. 14 is a schematic diagram illustrating tail vein injection of the carbon nanotube-based anticancer agents to a tumor animal model prepared by an embodiment of the present invention.

FIG. 14 is a schematic diagram illustrating tail vein injection of the carbon nanotube-based anticancer agents to a tumor animal model prepared by an embodiment of the present invention.

Figure 15:
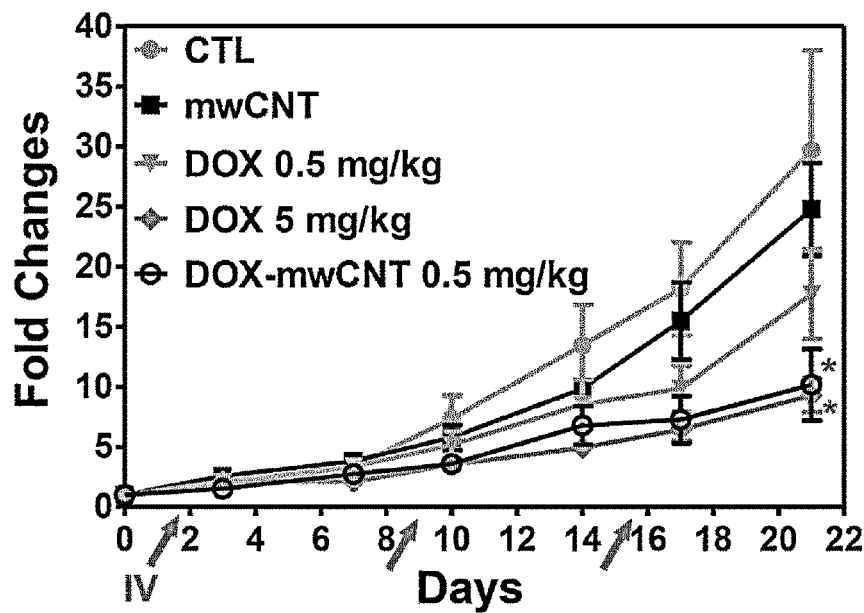
FIG. 15 is a graph representing the magnification of tumor size depending on elapse time after in vivo injection of mwCNT, pure doxorubicin (0.5 mg/kg and 5 mg/kg) and the carbon nanotube-based anticancer agent of the present invention (DOX-mwCNT-25, 0.5 mg/kg).

Twenty one day after the tail vein injection, the changes in tumor size of sacrificed animals were determined. As a result, as shown in FIG. 15, volume and mass of tumors treated with 0.5 mg/kg of DOX-mwCNT-25 were compatible with tumor mass of 5 mg/kg of pure DOX after three times I.V. injection. In contrast, no notable tumor inhibition was observed on 0.5 mg/kg of pure DOX.

Furthermore, after the administration of the anticancer agent, tumor tissues taken from the sacrificed animals were weighed. In this case, in order to compare the significance of each group, Prism (GraphPad Software, Inc.) was used for statistical analysis with one-way ANOVA (analysis of variance) ( $P<0.01$, * $P<0.001$).

As a result, as shown in FIG. 15, tumor size of groups treated with doxorubicin and DOX-mwCNT-25 was reduced, and in the group treated with DOX-mwCNT-25, when even a low dose (0.5 mg/kg) was administered, the size of tumor tissue was decreased significantly compared to non-treated control group. On the other hand, in the case of doxorubicin, the size of tumor tissue was decreased significantly compared to the control group only when a large amount of dose (5 mg/kg) was used.

Figure 16:
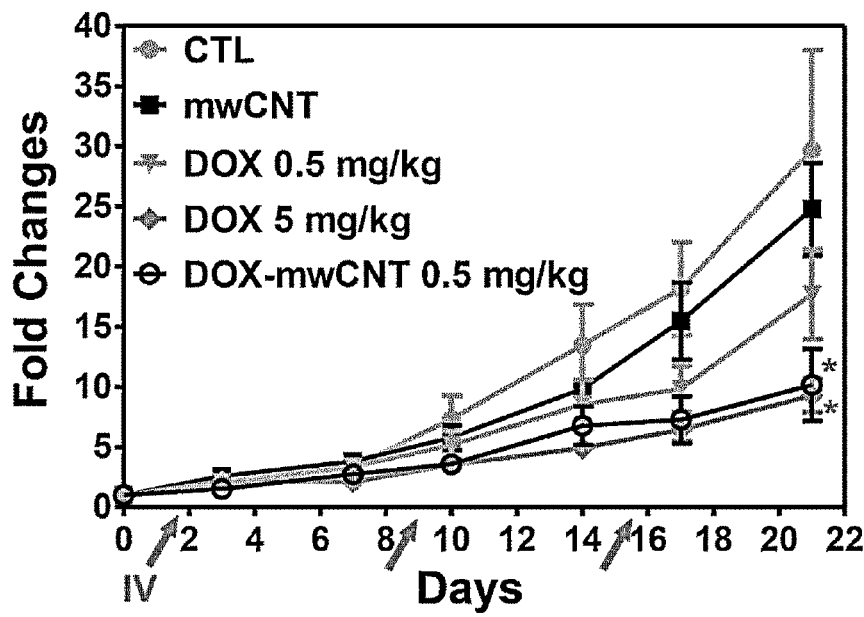
FIG. 16 is a graph representing weights of tumor tissues taken from tumor model animals sacrificed after in vivo injection of mwCNT, pure doxorubicin (0.5 mg/kg and 5 mg/kg) and the carbon nanotube-based anticancer agent in accordance with an embodiment of the present invention (DOX-mwCNT-25, 0.5 mg/kg).
Figure 17:
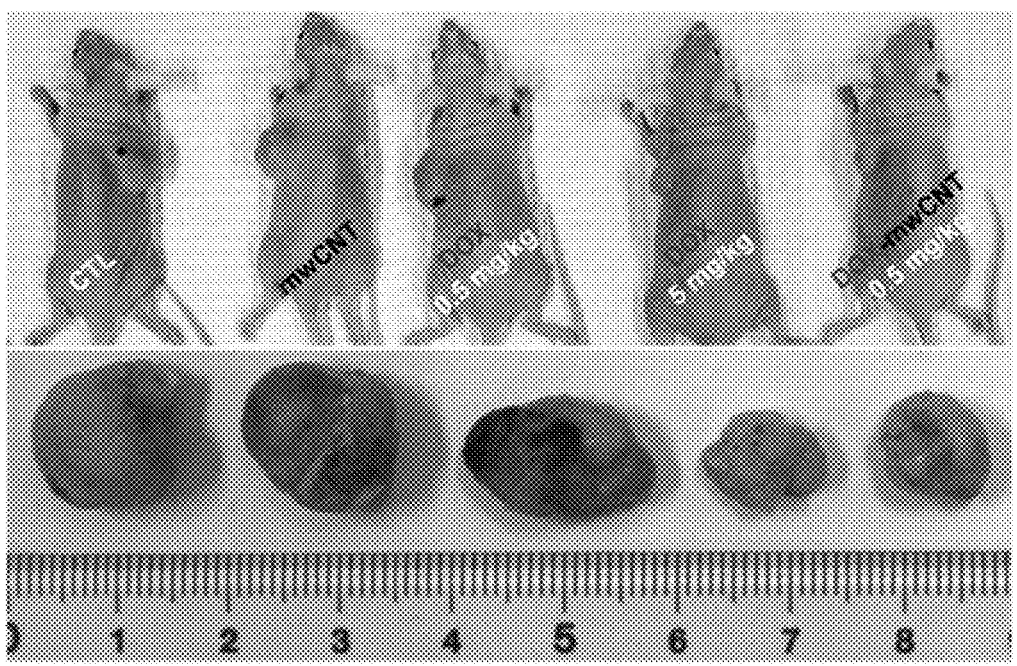
FIG. 17 is a series of photographs taking tumor model animals sacrificed (top) and tumor tissues therefrom (bottom) after in vivo injection of mwCNT, pure doxorubicin (0.5 mg/kg and 5 mg/kg) and the carbon nanotube-based anticancer agent in accordance with an embodiment of the present invention (DOX-mwCNT-25, 0.5 mg/kg).

Moreover, these results were similar with FIGS. 16 and 17 showing the change of the size and shape of tumor tissues isolated from each group. It tended that tumor size was decreased in the groups administrated with DOX and the carbon nanotube-based anticancer agent, respectively, and the size and shape of tumor tissues taken from the animal administrated at a high dose of DOX (5 mg/kg) was similar to those from the animal administrated at a low dose of DOX-mwCNT-25 (0.5 mg/kg) (FIGS. 16 and 17).

Figure 18:
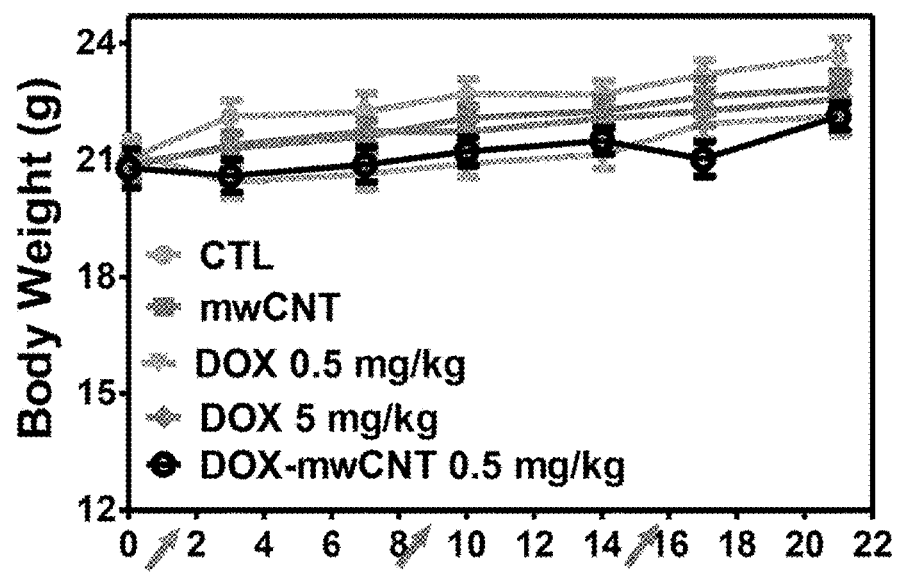
FIG. 18 is a graph recording body weights of tumor model animals after in vivo injection of mwCNT, pure doxorubicin (0.5 mg/kg and 5 mg/kg) and the carbon nanotube-based anticancer agent in accordance with an embodiment of the present invention (DOX-mwCNT-25, 0.5 mg/kg).

On the other hand, the animals used in the above-described experiments showed no significant weight change (FIG. 18).

Tumor killing activity corresponding to one achieved by administrating a high dose of doxorubicin was shown upon administrating even a low dose (about 1/10 of the doxorubicin) of the carbon nanotube-based anticancer agent according to an embodiment of the present invention. Therefore, the anti-cancer agent according to an embodiment of the present invention can be expected to have superior anticancer effect, while capable of avoiding the toxic side effects of doxorubicin itself.

2-2: Histopathological Observation of Tumor Tissues

Two weeks after transplanting breast cancer cells to BALB/c nude mice, the carbon nanotube-based anticancer agent according to an embodiment of the present invention was administered, and the mice were observed for 24 days. Then, the present inventors anesthetized the mice with ethyl ether, sacrificed them and collected tumor tissues therefrom. After measuring the weight of the collected tumor tissues, the tumor tissues were fixed for 24 hours in 10% formalin, washed with water and dehydrated and dipped in 70, 80, 90, 95 and 100% of ethanol, serially. The tissues were transparentized with xylene and embedded in paraffin. And then the embedded tissues were sliced at a thickness of 5 um, placed on glass slides. The tissue slides were applied to Haematoxylin-Eosin staining and the stained slides were observed with an optical microscope.

Figure 19:
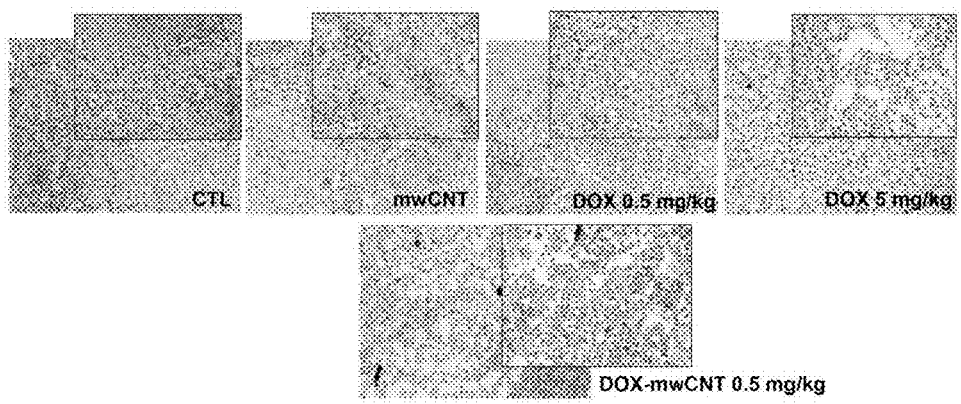
FIG. 19 is a series of microscopic images showing histological analyses of tumor tissues taken from tumor model animals sacrificed after in vivo injection of mwCNT, pure doxorubicin (0.5 mg/kg and 5 mg/kg) and the carbon nanotube-based anticancer agent in accordance with an embodiment of the present invention (DOX-mwCNT-25, 0.5 mg/kg).

As a result, as shown in FIG. 19, tissues taken from groups administrated with a low dose (0.5 mg/kg) and a high dose (5 mg/kg) showed increased necrosis compared to control group (Cont.) and a plentiful of punctures within tissues reflecting the necrosis were observed. On the contrary, anticancer effect of the group administrated with the DOX-mwCNT-25 according to an embodiment of the present invention was significantly superior to that of the doxorubicin-treating group. On the other hand, animals treated only with PBS or mwCNT did not show any damage of the tumor tissues (FIG. 19). These results, as well as the results confirmed from FIGS. 15 to 18, proved that the carbon nanotube-based anticancer agent according to an embodiment of the present invention has excellent anti-cancer effect to tumor cells, and lowers side effects due to toxicity of drug itself in comparison with a doxorubicin single drug.

EXPERIMENTAL EXAMPLE 3

In Vivo Distribution of Carbon Nanotube-based Anticancer Agent after the Administration The present inventors analyzed in vivo distribution of the carbon nanotube-based anticancer agent according to an embodiment of the present invention after in vivo administration.

Particularly, DOX-mwCNT-25 according to an embodiment of the present invention or doxorubicin were administrated at a dose of 2 mg/kg to tumor model BALB/c nude mice via I.V. injection and the mice were sacrificed 30 min and 6 hours after the administration. And then tumors, hearts, lungs, spleens, kidneys, stomachs, small intestines and blood samples were taken and amount of doxorubicin was measured. Blood samples were dissolved in a lysis buffer comprising 1% SDS, 1% Triton X-100, 40 mM Tris-acetate, 10 mM EDTA, and 10 mM DTT, and incubated with isopropanol containing 0.75 M HCl for 15 hours at −20° C. and doxorubicin was extracted. The other tissues were grinded with a grinder after adding 0.5 ml of buffer solution containing 0.25 M sucrose, 40 mM Tris acetate and 10 mM EDTA. And then, 0.2 ml was mixed with 0.1 ml of 10% Triton X-100 and strongly agitated. The mixture was then incubated for 15 hours at −20° C. and doxorubicin was extracted. The doxorubicin extracted from each tissue sample was quantified using a plate reader.

Figure 20:
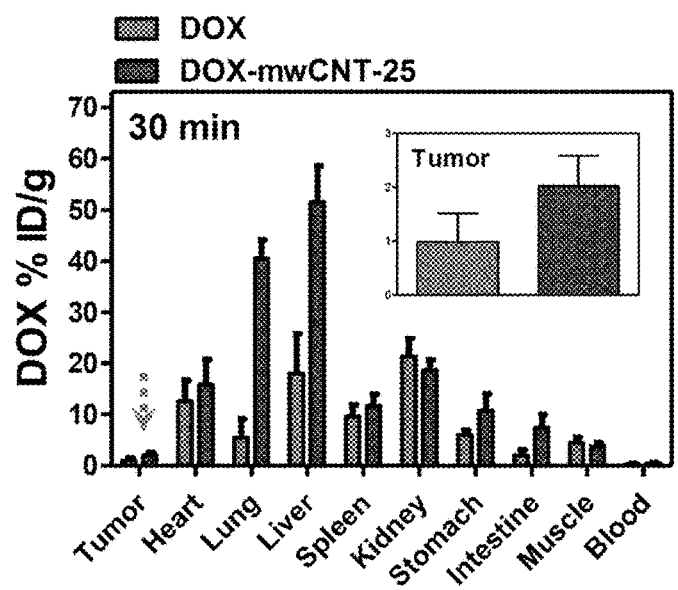
FIG. 20 is a graph representing the distribution of doxorubicin and DOX-mwCNT-25 in accordance with an embodiment of the present invention in various tissues and cancer tissues after 30 minutes of in vivo injection of the doxorubicin and the DOX-mwCNT-25.
Figure 21:
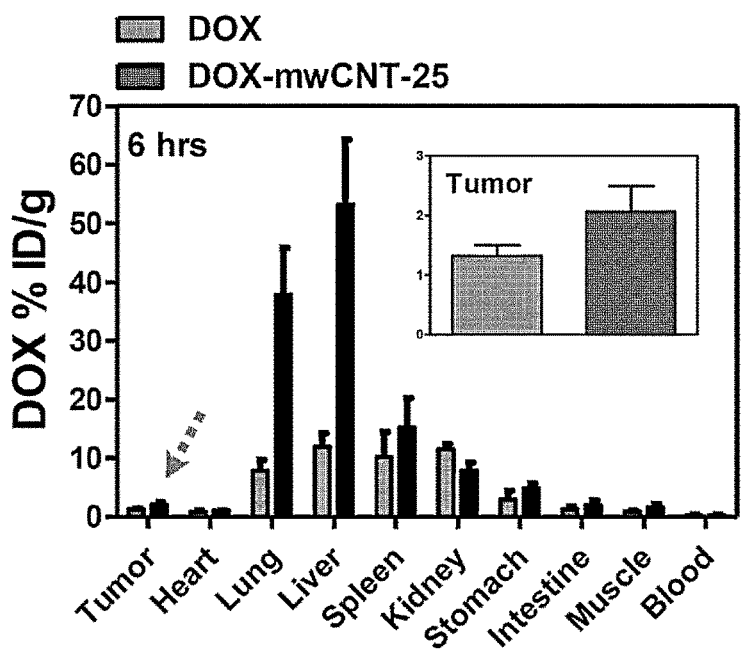
FIG. 21 is a graph representing the distribution of doxorubicin and DOX-mwCNT-25 in accordance with an embodiment of the present invention in various tissues and cancer tissues after 6 hours of in vivo injection of the doxorubicin and the DOX-mwCNT-25

As a result, as shown in FIGS. 20 and 21, more than 40% of DOX-mwCNT-25 was accumulated in the liver and lung after 30 min and 6 hours of tail vein injection. Heart, spleen, stomach, and intestine also showed greater accumulation of DOX-mwCNT-25, as compared to pure DOX after 30 min of I.V. injection. This tendency sustained for 6 h except in the heart (FIG. 21). The elevated blood flow in the heart may have accelerated the clearance rate of DOX-mwCNT from the heart by greater mechanical pumping. Accumulation rate of DOX-mwCNT to tumor tissues (2%) was same with previous studies.

EXPERIMENTAL EXAMPLE 4

Identification of Carbon Nanotube-based Anticancer Agent Through In Vitro Experiments Subsequently, the present inventors performed cytotoxicity assay using drugs with a concentration corresponding to the dose used for in vivo condition. This is because effective drug concentration in the tumor tissue depends on the allocation ratio from biodistribution of drugs. Based on the biodistribution after tail vein injection, only 1-2% of dosage reaches to the tumor tissue (FIGS. 20 and 21).

4-1: Confirmation of Anticancer Effect on Lung Cancer Cells

A549 cells (1×104 cells/well, CAT: CRL-1658, ATCC) were seeded in a 96-well plate and incubated with DMEM medium supplementing 10% FBS (fetal bovine serum). At this time, the culture was maintained under the condition of 5% of CO2 at 37° C. The cells were cultured for 24 h and mwCNT-COOH, EPI, EPI-EGF, EPI-mwCNT and EPI-EGF-mwCNT were treated to each well with ratios of 0.086, 0.172, 0.345, 0.69, 1.38 μmol/L, respectively and then further cultured for 48 h. And then, drug solutions were removed from the plate, 100 μl of MTT reagent (1 mg/ml, 3-(4,5-dimethylthiazol-2-yl)-2,5-diphenyltetrazolium bromide) was slowly added to each well, and incubated for 1 h at 37° C. Thereafter, 100 μl of DMSO solution per well was added, followed by measuring absorbance at 560 nm using a microplate reader (Model 680, Bio-Rad).

Figure 22:
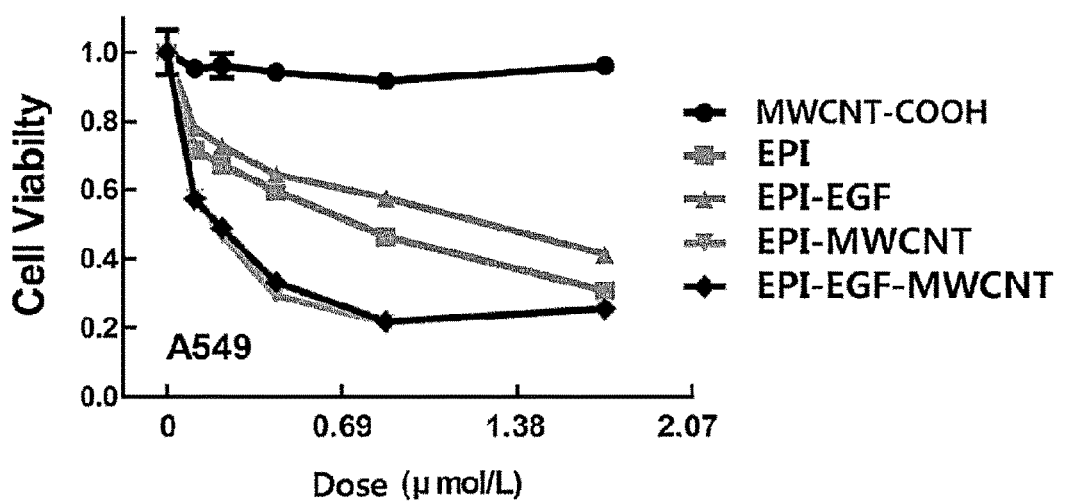
FIG. 22 is a graph representing anticancer effects of EPI-mwCNT in lung cancer cells.

As a result, as shown in FIG. 22, it was confirmed that groups treated with drugs containing epirubicin (EPI, EPI-EGF, EPI-mwCNT, and EPI-EGF-mwCNT) showed lower viability than the group treated with only carbon nanotube (mwCNT-COOH). In addition, among groups treated with drugs containing epirubicin, epirubicin bound carbon nanotubes according to embodiments of the present invention (EPI-mwCNT and EPI-EGF-mwCNT) showed more potent anticancer effect than pure epirubicin when a small amount (1 μM) was treated (FIG. 22).

Figure 23:
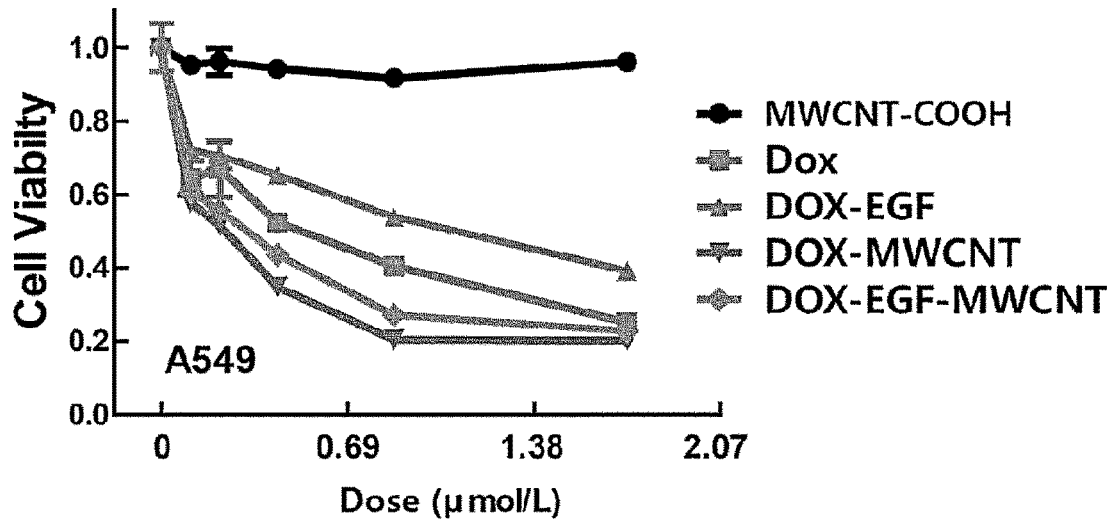
FIG. 23 is a graph representing anticancer effects of DOX-mwCNT in lung cancer cells.

Then, the present inventors treated drugs containing doxorubicin (DOX-EGF, DOX-mwCNT-25, DOX-EGF-mwCNT) to the same lung cancer cell A549. All the condition except drugs were same. As a result, doxorubicin-containing anticancer agents showed the most anticancer effect when doxorubicin was covalently attached to carboxylated carbon nanotubes, which was similar with the epirubicin-based anticancer agents (FIG. 23).

4-2: Confirmation of an Effects on Breast Cancer Cells

Then, the present inventors analyzed anticancer effect of the carbon nanotube-based anticancer agent according to an embodiment of the present invention on breast cancer cells.

MDA-MB-231 cells (5×10³ cells/well, Cat#: HTB-26, ATCC) were cultured in 96-well plates with DMEM supplemented with 10% of FBS in a humidified incubator at 37° C. with 5% of $CO_2$ level for 24 h. After the cultivation, mwCNT-COOH, doxorubicin and DOX-mwCNT-25 were treated to each well at concentrations of 100, 200, 400, 900, 1800, 3200 ng/ml, respectively and the cells were further cultivated for 48 h. And then, drug solutions were removed from the plate, 100 μl of MTT reagent (1 mg/ml) was slowly added to each well, and incubated for 1 h at 37° C. Thereafter, 100 μl of DMSO solution per well was added, followed by measuring absorbance at 560 nm using a microplate reader (Model 680, Bio-Rad).

Figure 24:
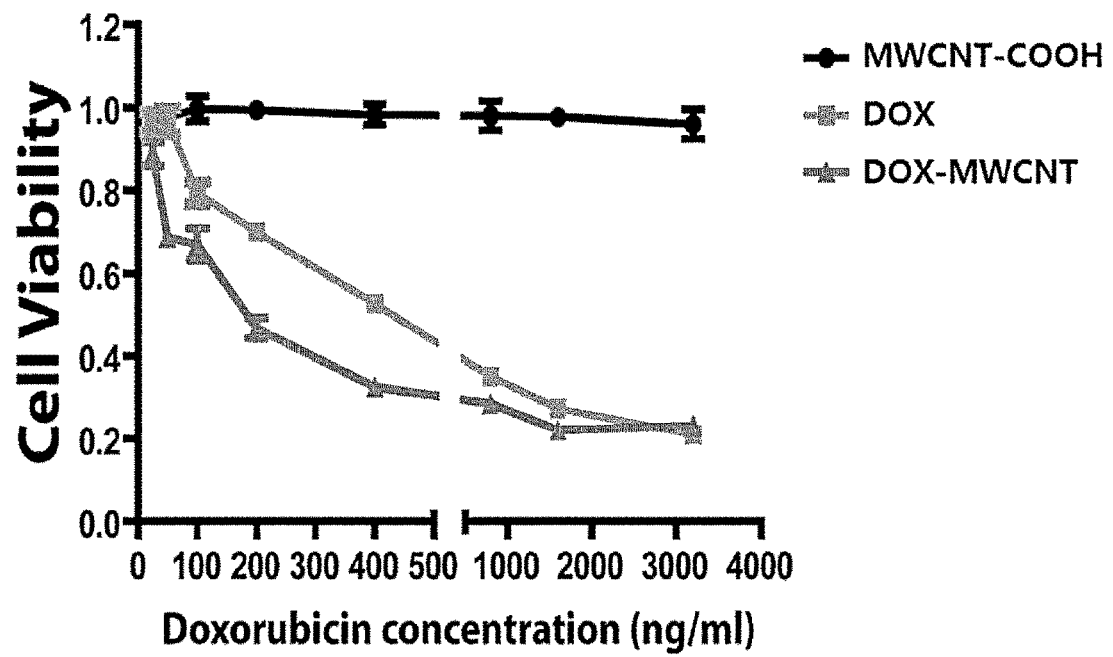
FIG. 24 is a graph representing anticancer effects of DOX-mwCNT in breast cancer cells.

As a result, as shown in FIG. 24, anticancer effect of the carbon nanotube-based anticancer agent, DOX-mwCNT-25 when treated at a concentration of 400 ng/ml was comparable to that of 1000 ng/ml of doxorubicin (FIG. 24).

Taken together, these results proved that the anticancer agent prepared using carboxylated carbon nanotubes according to an embodiment of the present invention provides potent anticancer effect even at a low dose corresponding to a high dose of a single anticancer drug. Further, these results suggest that any anticancer drugs having an amine group besides doxorubicin and epirubicin may be applied to the present invention.

EXPERIMENTAL EXAMPLE 5

Intracellular Uptake and Efflux of the Carbon Nanotube-based Anticancer Agent 5-1: Drug Release Rate DOX-mwCNTs was dissolved at a concentration of 1 μg/mL in PBS (pH 7.2) and acetate buffered saline (ABS, pH 5.0), and incubated for 1, 2, 5, 10, 24, 48, 72, 120, and 240 h, respectively in an incubator at 37° C. with agitating using a rocker. Each sample at the designated time was filtered using Amicon® Ultra Centrifugal Filters (50K Membrane, Millipore, Ireland) with 15,000 rpm for 15 min and fluorescence of supernatants was detected using a plate reader (emission at 590 nm; excitation at 470 nm).

Figure 25:
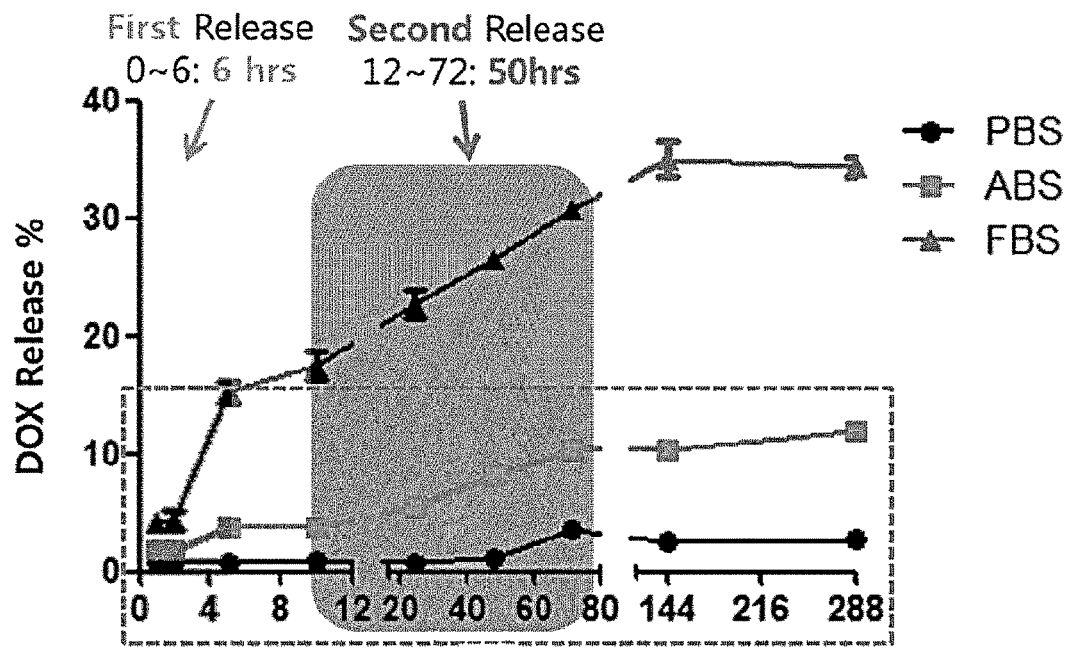
FIG. 25 is a graph showing the degree of release of doxorubicin from the DOX-mwCNT-25 according to one embodiment of the present invention which represents two rounds of drug release (the first release: 6 hours, and the second release: 50 hours) of doxorubicin from DOX-mw-CNT-25 in the blood (FBS, pH=7.2) and the interior of cells (ABS, pH=5), respectively.
Figure 25:
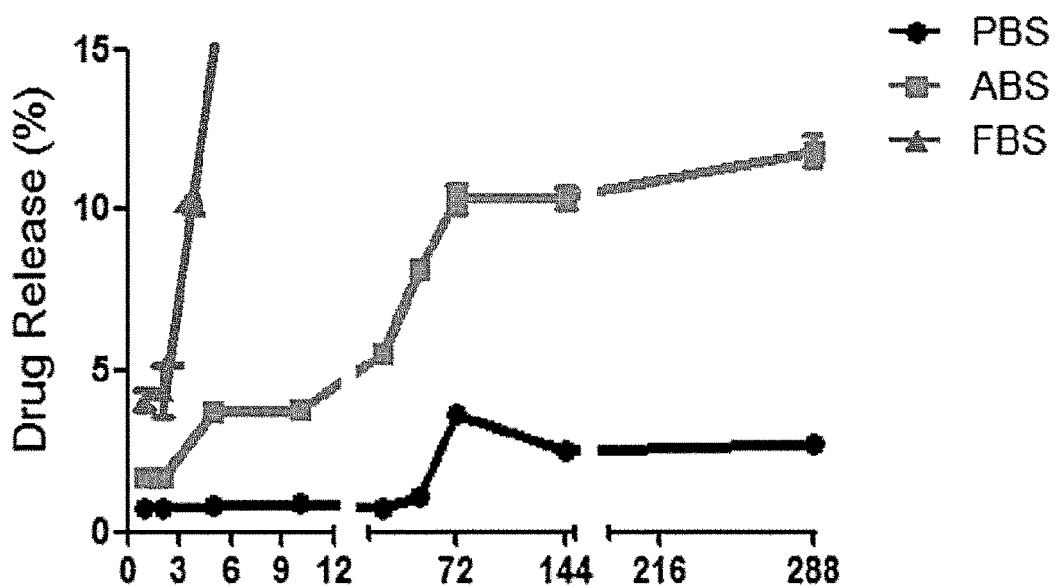

As a result, as shown in FIG. 25, it was confirmed that drugs were slowly released in two phases, 0-6 hours and 12 to 72 hours and the drug release rate was increase for 6 hours (first release) and 50 hours (second release). The second release (12~72 h) corresponds to proliferating time of cancer cells (12~48 h), and this means that the carbon nanotube-based anticancer agent according to an embodiment of the present invention provides significant anticancer effect by releasing anticancer drugs from carbon nanotubes at this time. In addition, the anticancer agent according to an embodiment of the present invention showed higher release rate in ABS than PBS, wherein PBS mimics in vivo environment with physiological pH (pH 7.0) and ABS mimics pH condition (pH 5.0) within lysosome which is the final stage of transport by endosome. Thus, these comparative analysis of drug release rate of DOX-mwCNT between ABS and PBS suggests that the DOX-mwCNT may be transferred to cells as a stable state and release drugs within cells after being administrated in vivo.

5-2: The Degree of Uptake within Cells and Efflux from the Cells

The present inventors observed the degree of uptake of the carbon nanotube-based anticancer agent within cells and the degree of efflux thereof from the cells according to concentration of the anticancer agents and treating time.

Figure 26:
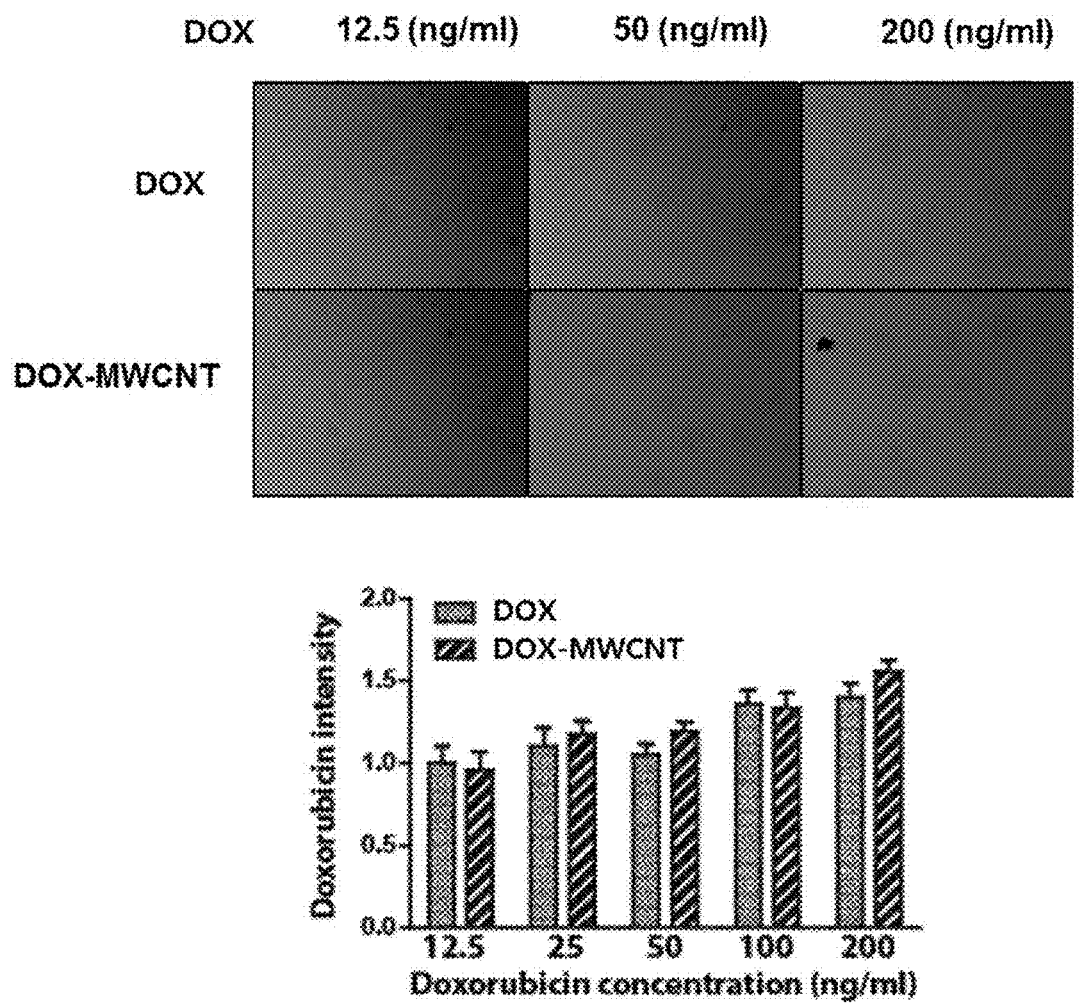
FIG. 26 is a photograph showing the degree of absorption of DOX-mwCNT-25 in accordance with an embodiment of the present invention after 2 hours of treatment of the DOX-mwCNT-25 to breast cancer cells (top) and a graph representing the results of the analysis (bottom).

MDA-MB-231 cells ($1\times10^4$ cells/well) cultivated in 24 well plate were treated with DOX-mwCNTs according to an embodiment of the present invention and doxorubicin at concentrations of 12.5, 25, 50, 100, and 200 ng/ml. Two hours after the treatment the cells were fixed and images were taken using a fluorescent microscope with 594 nm of excitation wavelength (FIG. 26). Since doxorubicin is a fluorophore, amount of uptaken doxorubicin by cells was calculated as intensity of fluorescence detected. In FIG. 26, the degree of uptake and the degree of efflux were compared according to concentrations of drugs to be treated. The intensities of fluorescence were proportional to the concentration of drugs to be treated in the DOX-mwCNT treating group and DOX treating group, and there is no significant difference between the two groups (FIG. 26).

Figure 27:
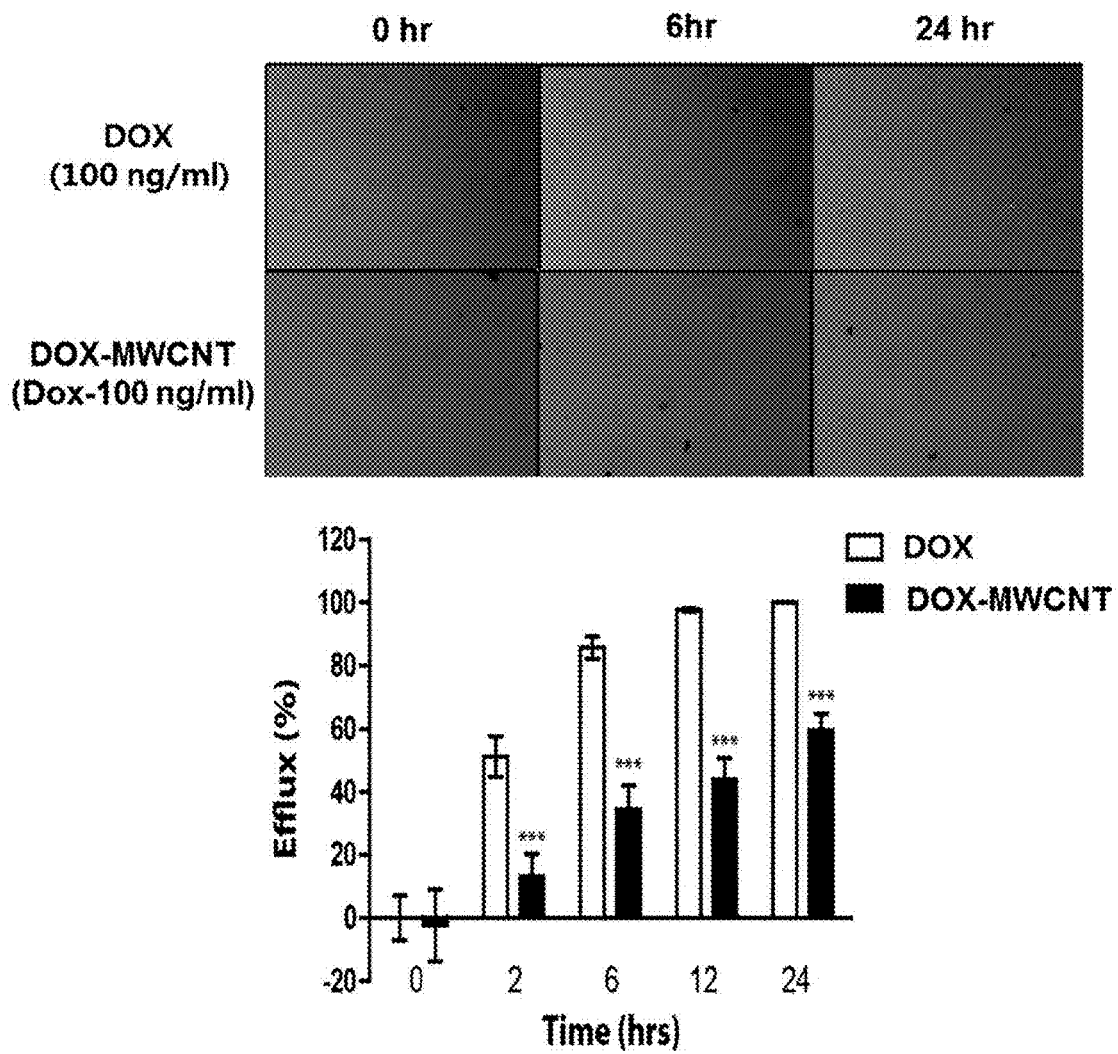
FIG. 27 is a photograph showing the degree of efflux of DOX-mwCNT in accordance with an embodiment of the present invention compared with doxorubicin over time (2-24 hours) after removing drugs 2 hour after treating the DOX-mwCNT and doxorubicin to breast cancer cells.

In addition, for efflux analysis, MDA-MB-231 cells ($1\times10^4$ cells/well) cultivated in 24 well plate were treated with 100 ng/ml of DOX-mwCNT according to an embodiment of the present invention and doxorubicin, respectively. Two hours after the treatment, culture media was removed and the cells were washed three times with PBS and incubated with regular culture medium containing no anticancer agents for 24 h. Then the degree of efflux of doxorubicin from the cells was observed using a fluorescent microscope (FIG. 27). As a result of incubating the cells for 0, 2, 6, 12, and 24 h in regular media, 40% of DOX-mwCNT-25 was retained within MDA-MB-231 cells after 24 hours of incubation whereas pure doxorubicin was completed excreted from the MDA-MB-231 cells within 6~12 hours (FIG. 27). Such a difference was even bigger, as the concentration of drugs to be treated was increased. In the experiment, zero time (0 h) means a time when 2 hours has elapsed after removing doxorubicin and washing cells with PBS.

This result proves that since the carbon nanotube-based anticancer agent according to an embodiment of the present invention is linked to carbon nanotubes strongly via covalent bond, it nullifies efflux of anticancer drugs from cancer cells due to drug resistance thereby, and thus it's retention time in cancer cells is long and it releases anticancer drugs continuously during proliferating phase of cancer cells. In other words, the carbon nanotube-based anticancer agent according to an embodiment of the present invention may enhance therapeutic effect of anticancer drugs with a very small amount, and may maximize therapeutic effect against drug-resistant cancers.

Furthermore, the present inventors performed a high resolution image analysis for 24 h in order to investigate the degradation of uptaken doxorubicin signal by co-staining doxorubicin and late endosome specific marker. With a high resolution fluorescence microscopic observation, few late endosomes were observed after removal of doxorubicin from nucleus (FIG. 28A). Therefore, it was understood that late endosomes act as transporters of doxorubicin excreted from nucleus. On the contrary, cells treated with DOX-mwCNT-25 for 24 h did not show reduced late endosome signal (FIG. 28B).

Figure 28:
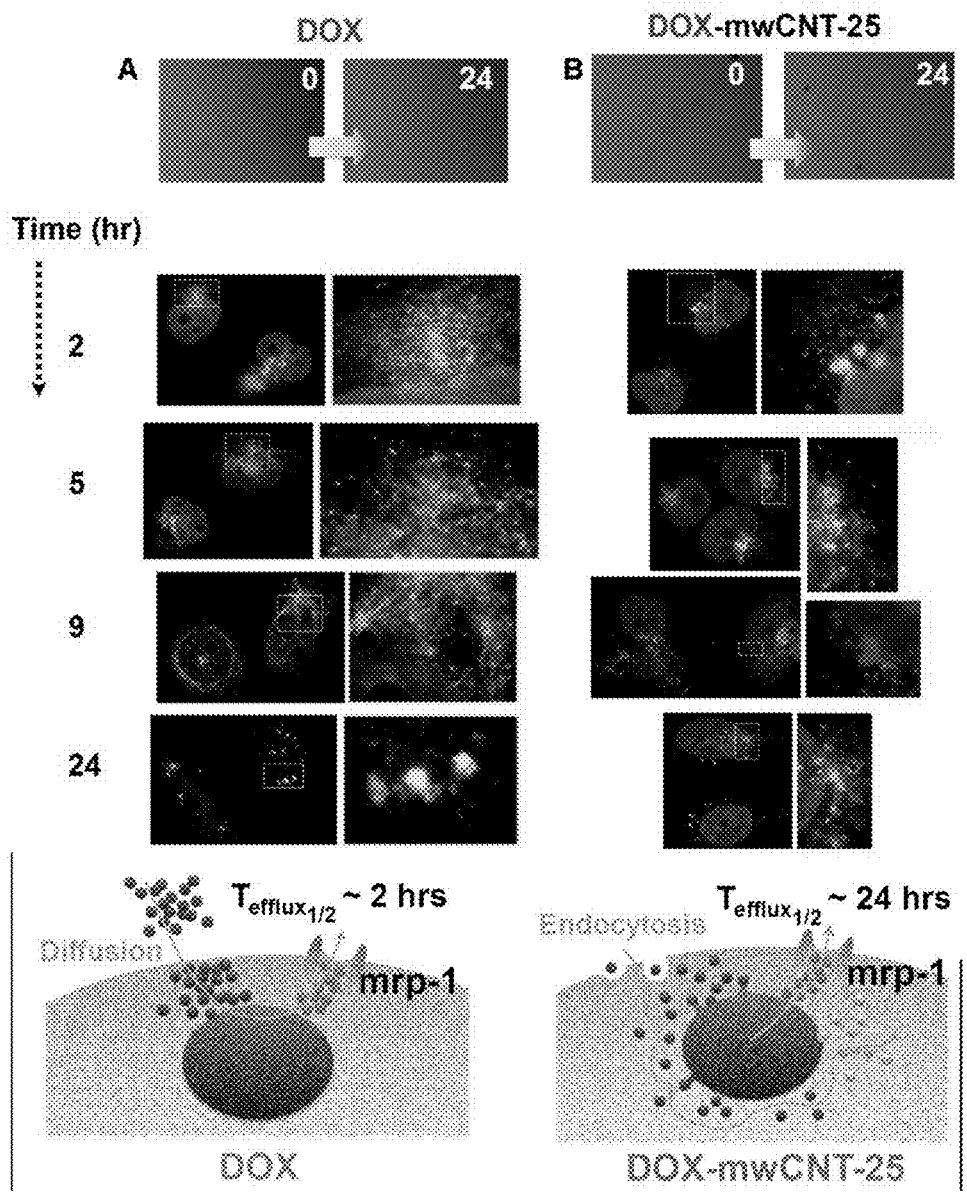
FIG. 28 is a series of fluorescent microscopic images representing the efflux procedure of pure doxorubicin from MDA-MB-231 cells after 2-24 hours of treatment of doxorubicin (A) and the inhibition of efflux of DOX-mwCNT in accordance with an embodiment of the present invention from MDA-MB-231 cells after 2-24 hours of treatment of the DOX-mwCNT (B), and schematic diagrams for describing the difference of corresponding mechanisms (bottom).

Furthermore, a respectable amount of early endosomal vesicles surrounding DOX-mwCNT-25 were fused to nucleus after 24 h. This was the first finding that endosomal vesicles surrounding DOX-mwCNT-25 approach to nucleus continuously via endosomes or late endosomes and release doxorubicin for 24 h even after 2 hour of exposure of DOX-mwCNT-25 (FIG. 28).

5-3: Analyzing Pumping Action of Cancer Cells

To determine whether the carbon nanotube-based anticancer agent according to an embodiment of the present invention has a therapeutic effect against cancer cells resistant to anticancer drugs, the present inventors analyzed the degree of expression of Mrp-1 (multiple drug resistance protein 1). Mrp-1 gene has been known to be overexpressed in cancer cells showing multi drug resistance and therapeutic effect of MRP-1 substrate-type drugs was increased by inhibiting Mrp-1 gene (Kuss, B. J. et al., *Int. J. Cancer*, 98: 128-133, 2002).

MDA-MB-231 breast cancer cells ($4\times10^5$ cells/well) known to overexpress MRP1 were plated in a 6 well plate and 100 ng/ml of doxorubicin and DOX-mwCNT were treated to the cells for 2 h, respectively. Carbon nanotube as a control was treated with a concentration of 348 ng/ml for 2 h.

Two hours after treatment, culture mediums were replaced with DMEM medium supplemented with 10% FBS and not containing mwCNT, DOX, and DOX-mwCNT, and the cells were further incubated. Then RNA was isolated from cells after 2, 6, 12, 24, and 36 hours of incubation, respectively and then Mrp-1 mRNA level was analyzed. In this case, TRIZOL reagent (Invitrogen, USA) and chloroform were used for RNA isolation, then the isolated RNA was reacted with same volume of isopropanol for 2 h, quantified and subjected to RT-PCR (reverse transcriptase PCR).

Figure 29:
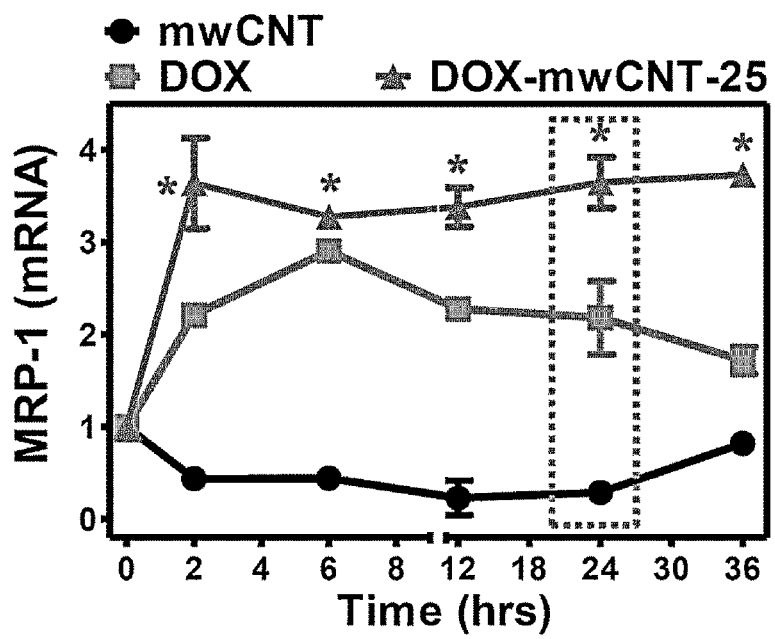
FIG. 29 is a graph representing non-efflux effect of the CNT-based anticancer agent according to an embodiment of the present invention through analyzing Mrp-1 (functioning in cancer drug pumping protein) mRNA expression levels.

As a result, as shown in FIG. 29, expression of Mrp-1 gene in cells was decreased after 6 hours of treatment of doxorubicin, whereas the expression of Mrp-1 gene in the DOX-mwCNT treating group sustained continuously.

Figure 30:
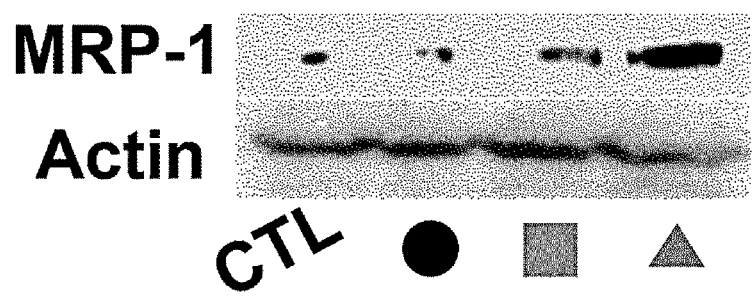
FIG. 30 is a photographs representing the result of western blot analysis investigating the expression level of MRP-1 protein in order to confirm the non-efflux effect of the CNT-based anticancer agent according to an embodiment of the present invention.

To confirm the above result in protein level, the present inventors performed western bot analysis of the MRP-1 protein, there was a significant difference in protein expression of MRP-1 between doxorubicin- and DOX-mwCNT-25-treating groups (FIG. 30). In particular, the pure doxorubicin-treating groups showed a weak band at 24 hours after the treatment, whereas the DOX-mwCNT-25-treating group sustained an upregulated expression of MRP-1. Despite of previous studies reporting that Mdr-1 and Mrp-1 genes mediate drug resistance of MDA-MB-231, Mdr-1 was hardly detected in this experiment due to short drug exposure time (2 hours).

The above result proves that the expression of MRP-1 was maintained instead of being decreased in order to pump out anticancer drugs according to continuous excretion of the carbon nanotube-based anticancer agent in accordance with an embodiment of the present invention from breast cancer cells. That is, it is suggested that the carbon nanotube-based anticancer agent in accordance with an embodiment of the present invention provides therapeutic effect against cancer for a long time, because it release anticancer drugs from carbon nanotubes continuously.

EXPERIMENTAL EXAMPLE 6

Drastic Drug Release Under the Condition of Late Endosome-lysosome Delivery and Acidic Lysozyme Investigating initial pathway of a series of phagocytosis is essential to understand the drug delivery at the intracellular level. The advantage of the mechanism of endosome delivery of DOX-mwCNTs generally is that this type of particle does not experience the drug efflux from the cytoplasm to the extracellular space. If a late endosome marker is analyzed, it is possible to observe DOX-mwCNTs uptaken before transporting them to lysosome or Golgi body directly, this is because late endosomes are positioned between early endosomes (corresponding to approaching drugs) and lysosome (corresponding to degrading drugs). Previous studies have recited possibility of drug delivery through endosome and lysosome, but there is no evidence that endosome or lysosome is the exact site where the drugs are released.

Figure 31:
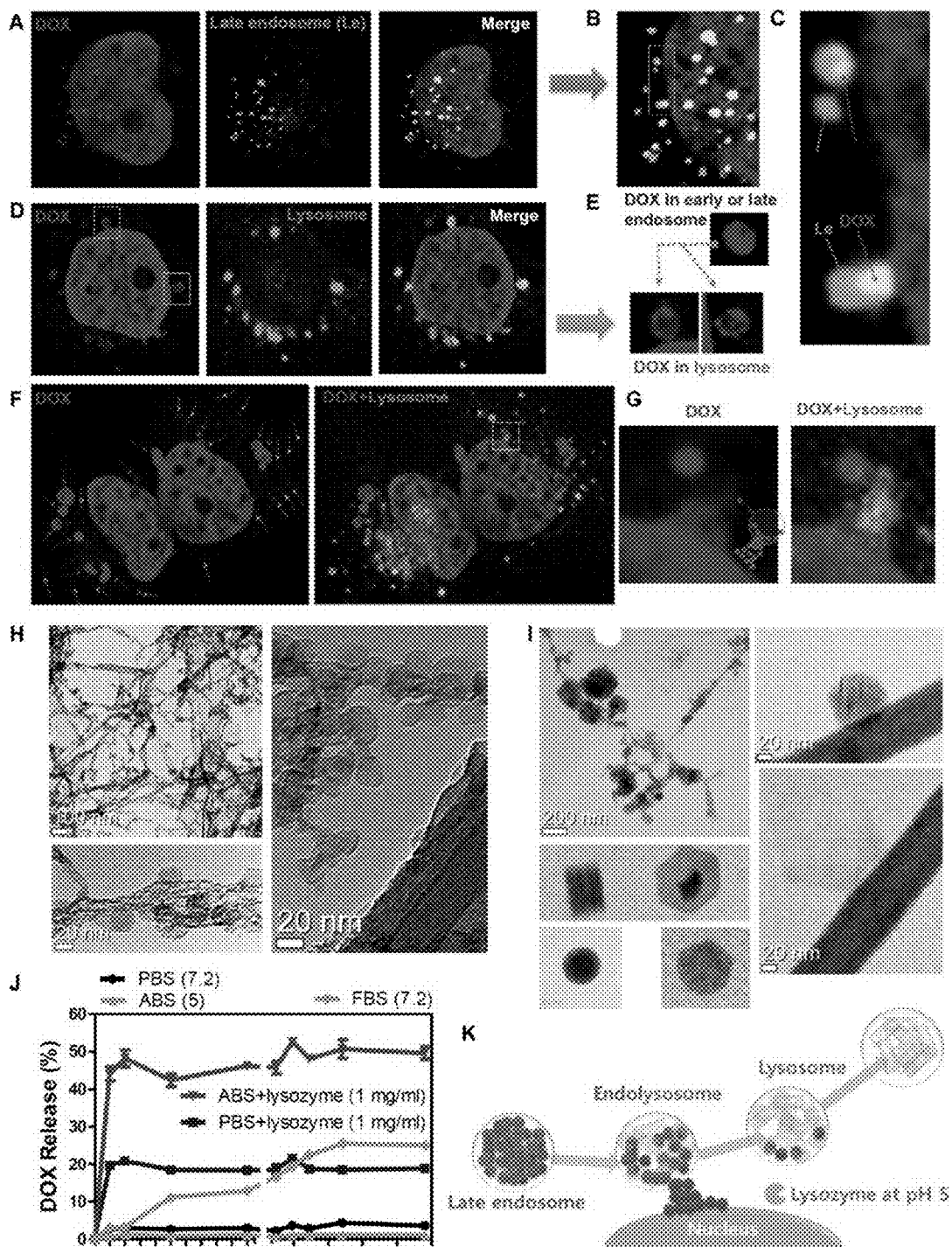
FIG. 31 represents drastic efflux of doxorubicin after transferring to late endosome-lysosome under acidic lysosomal condition, A is a series of fluorescent microscopic images representing co-staining of doxorubicin (red) and late endosome, B is a magnified image showing late endosomes approaching to a nucleus of a cancer cell and late endosomal vesicles fused to the nucleus, C is a high resolution image representing the diffusion of doxorubicin (yellow) from late endosomes (green) to the nucleus (red), D to F are a series of fluorescent microscopic images representing co-stained doxorubicin (red) and lysosomes (green) overlapping directly surrounding cancer nucleus, G is a magnified image showing the diffusion of doxorubicin from lysosomal vesicles, H is a series of cryo-TEM images showing covalently linked DOX on mwCNTs corresponding to vesicles until late endosome stage, I is a series of cryo-TEM images showing removed DOX by cleaving amide bond through lysozymes and attachment of lysozymes on mwCNTs (instead of DOX), corresponding to vesicles after lysosome stage, J is a graph representing drug release in buffer solutions with different pH (pH 5 and 7.2), and FBS and in case of treating lysozyme (1 mg/ml) in buffer solution with different pH. J is a graph representing the stability of DOX from covalently conjugated mwCNT during endolysosome pathway, K is a schematic diagram illustrating drug delivery pathway of a drug covalently linked to carbon nanotube through endo-lysosome pathway.

The present inventors proved that late endosomes play a key role in drug release of the DOX-mwCNT-25 according to an embodiment by observing an endosome marker and doxorubicin using a high resolution microscope (A to G of FIG. 31).

A to G of FIG. 31 provides evidences of drug release during endosome-lysosome stages, this is because doxorubicin is abundant in the late endosome but, deficient in lysosome. As shown in a magnified microscopic image of late endosomes, the diffusion of doxorubicin from late endosome to nucleus (C of FIG. 31). This is the first evidence of release of doxorubicin from nanoparticles surrounded by late endosomes. As shown in microscopic images taking doxorubicin and lysosome, it is confirmed that approaching endosomes (red: doxorubicin within early or late endosomes) and lysosomes (green) heading to the outside of the cell containing reduced doxorubicin in lysosomal vesicles (G to F of FIG. 31). Through a magnified microscopic image, the diffusion of doxorubicin from lysosomal vesicles was identified (G of FIG. 31). Because more lysosomes were found in the vicinity of nucleus, a plentiful of acid hydrolyzing enzymes contained in late endosomes and lysosome surrounding nucleus have a sufficient enzymatic activity to cleave amide bonds between doxorubicin and mwCNT.

To understand the observed phenomenon, in vitro drug release experiments were performed to understand the burst release of DOX from covalently conjugated mwCNT during endolysosome pathway. First, outer cell environments (PBS) showed no distinct release of DOX as time advance (i.e., up to 240 h) (J of FIG. 31). DOX release in 10% FBS showed incremental release of DOX over time, suggesting that DOX-mwCNT bonds were slowly degraded across many hours under hematological environments (J of FIG. 31). Furthermore, linkages of designed drugs were highly stable in both neutral and acidic condition (J of FIG. 31). Thus, drug release analysis presents a designed DOX-mwCNT anticancer drug that is highly stable under extracellular conditions. Furthermore, drug release under intracellular conditions was also examined. Remarkably, notable release in high lysozyme density in neutral condition (pH=7) was observed and significant burst release was achieved by simultaneous exposure to an acidic environment and greater lysozyme density (J of FIG. 31). The observed release supported the observation that optimized conditions for cleaving covalently linked DOX to mwCNTs requires acidic hydrolase. Considering late endosomes and lysosomes are composed of 40 types of acidic hydrolases, including lysozymes, the obtained data provided evidence of a highly selective release of DOX during late endosome and lysosome stages. Lastly, cryo-TEM images showed evidence of DOX cleave from mwCNT and lysozyme attachment onto mwCNTs (H and I of FIG. 31). Various shapes corresponding to lysozyme crystallizations were identified by diffraction patterns in Cryo-TEM images (I of FIG. 31). Importantly, it was concluded that developed DOX-mwCNT-25 induced many endosomal vesicles compared to DOX and DOXIL and, thus, provided a more favorable condition than conventional drugs (DOX and DOXIL) for nullifying efflux working system of tested cancer cells. K of FIG. 31 a schematic diagram illustrating drug delivery pathway of a drug covalently linked to carbon nanotube through endolysosome pathway.

EXPERIMENTAL EXAMPLE 7

Cytotoxicity of the Carbon Nanotube-based Anticancer Agents 7-1: Evaluation of Safety Using Cytokines and Liver Enzymes The concentration of cytokines and liver enzymes were quantified after administrating the carbon nanotube-based anticancer agent according to an embodiment of the present invention to tumor model animals prepared in Example 2, in order to evaluate safety of the anticancer agent.

Specifically, the tumor model animals of the Example 2 were administrated with doxorubicin or DOX-mwCNT at a lower dose (0.5 mg/ml) or a high dose (5 mg/kg), 2 days after the administration, blood was collected, TNF-alpha, IFN-gamma, IL-2, IL-4, IL-6, GOT and GPT were quantified (requested to Green Cross Corp., Korea). As a control group, a blood sample of mice administered with PBS only was used. Performed experimental procedure is as follows: Before excising tumors and organs from mice sacrificed in Example 3, blood from the right ventricle was collected by 500 μl for each subject, and transferred to a vacuum tube (vacutainer) and centrifuged for 15 minutes at 3,000 rpm to separate plasma. And then, the plasma samples were frozen at −20° C. and the quantifying analyses were requested to the Medical Genomics Research Institute of Green Cross Corp.

Figure 32:
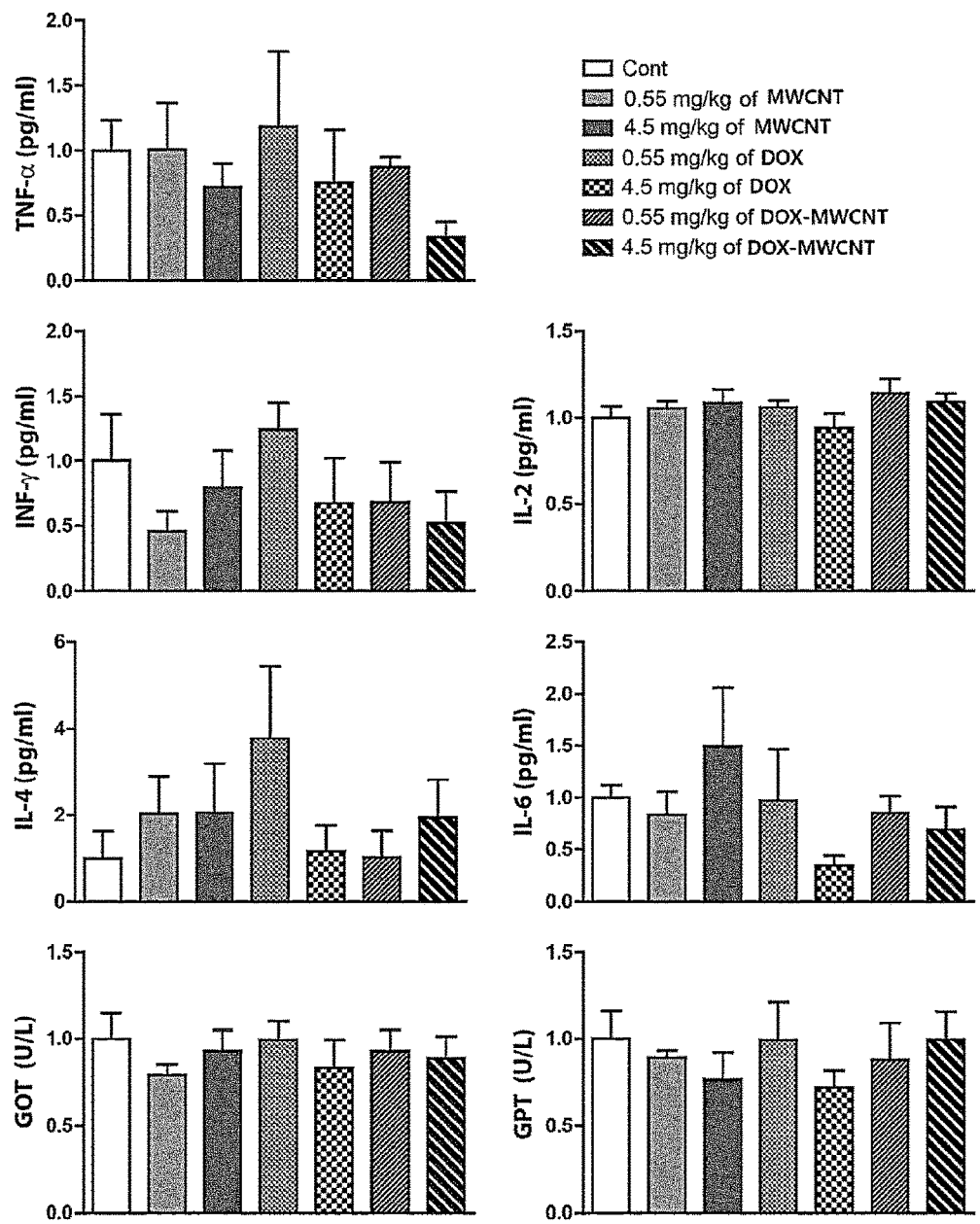
FIG. 32 is a series of graphs representing results of analyses of expressions of cytokines and liver enzymes after the administration of DOX-mwCNT, a CNT-based anticancer agent in accordance of an embodiment of the present invention to a tumor model animal prepared by xenotransplantation of breast cancer cells.

As a result, as shown in FIG. 32, it was confirmed that the group administered with the carbon nanotube-based anticancer agent according to an embodiment of the present invention showed similar or lower expression levels of the cytokines than a control group. Moreover, it was possible to confirm the safety of the carbon nanotube-based anticancer agent according to an embodiment of the present invention from the expression level of GOT and GPT, liver enzymes.

7-2: Liver Clearance Test

Figure 33:
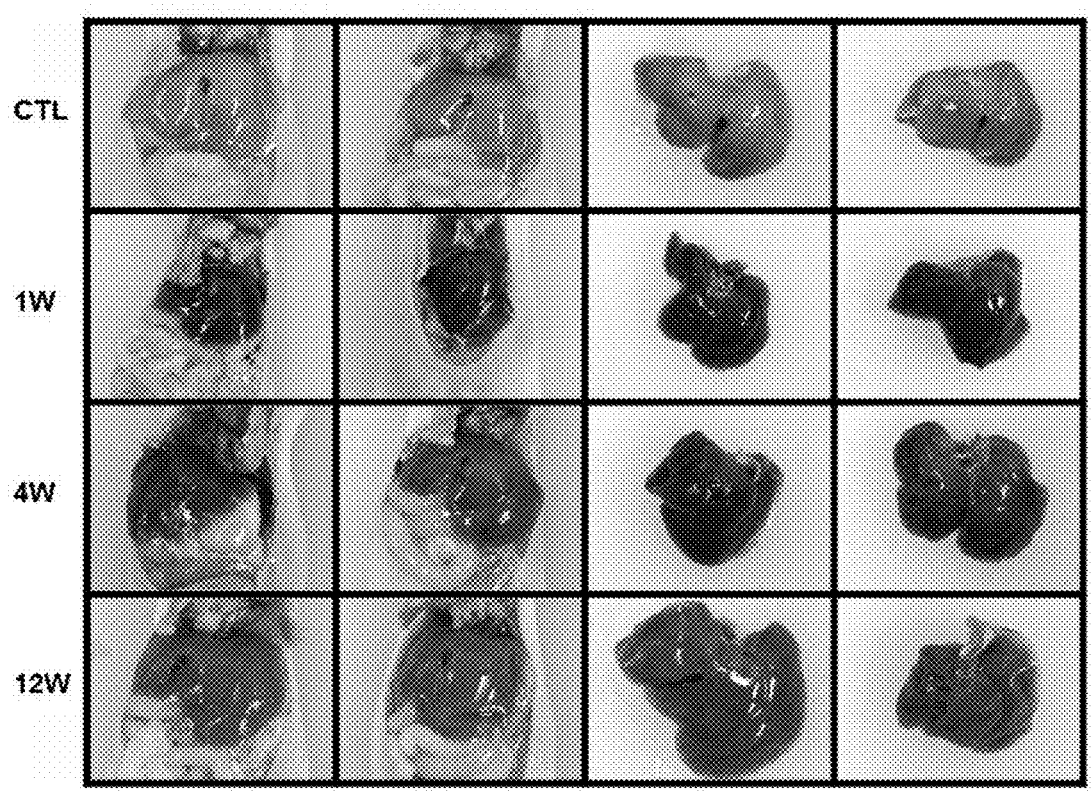
FIG. 33 is a series of photographs of livers taken from normal mice sacrificed after designated time of the administration of carbon nanotubes in order to determine liver clearance.

BALB/c nu/nu (athymic nude) mice injected with mwCNT at a dosage of 10 mg/kg were sacrificed after 1, 4, and 12 weeks. Then the sacrificed animals were applied to laparotomy, and organs thereof were observed. As a result, carbon nanotubes were accumulated in the lung and liver. However, residual amount of mwCNTs in liver was decreased with the lapse of time (1, 4 and 12 weeks) (FIG. 33).

Then, the present inventors investigate the degree of damage of liver tissue where the carbon nanotubes were distributed in concentration utilizing Haematoxylin-Eosin staining. Liver tissue was fixed for 24 h in 10% formalin, washed with running water and dehydrated with 70, 80, 90, 95, and 100% ethanol, sequentially. Thereafter, the dehydrated liver tissue was transparentized with xylene and embedded in paraffin. The embedded liver tissue was sliced with a thickness of 5 μm and the slice was placed on a glass slide glass. The slide was stained with haematoxylin and eosin staining reagent and taken images using an optical microscope.

Figure 34:
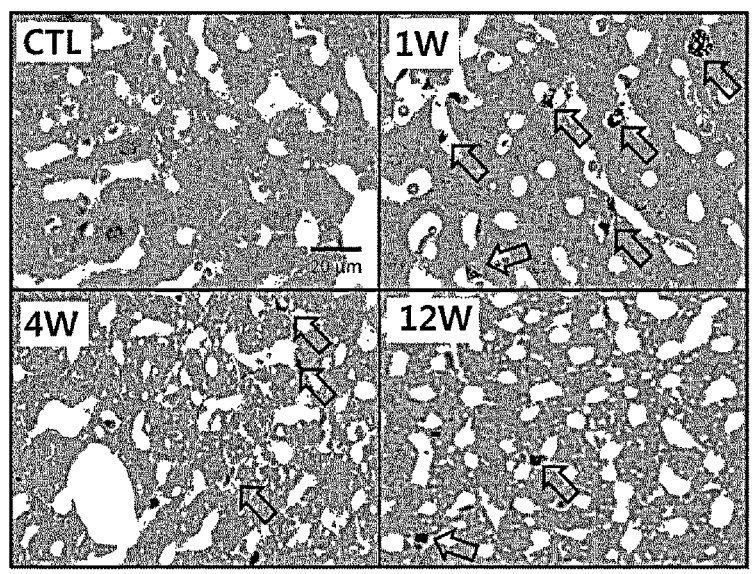
FIG. 34 is a series of histological images of tissue slices of the livers of FIG. 33 stained with haematoxylin-eosin.

As a result, as shown in FIG. 34, liver tissue treated with mwCNT has residual carbon nanotubes, and black spots were observed. However, the amount of the residual mwCNTs was decreased over time (FIG. 34). This result proves that the concentrated distribution and residence of carbon nanotubes in the liver and lung can be resolved by liver clearance over time. Also, since the degree of liver damage was very insignificant compared to the extent that mwCNT is intensively distributed in liver tissue, it means that the carbon nanotube-based anticancer agent in accordance with an embodiment of the present invention does not cause in vivo toxicity problems.

In summary, the present invention proved that the carbon nanotube-based anticancer agent according to an embodiment of the present invention can show therapeutic effect against cancer cells resistant to conventional anticancer drugs as well as show therapeutic effects with very small amount of dose compared with a single anticancer drug and thus lower side effects of anticancer drugs due to cytotoxicity. The carbon nanotube-based anticancer agent according to an embodiment of the present invention can provide anticancer effect even with a small amount (1/10 of single doxorubicin). This is because it releases anticancer drugs slowly for a long time via strong covalent bond which causes conformational change of doxorubicin. Also, since this sustained release of anticancer drugs within cancer cells can solve drug resistance problem which effluxes anticancer drugs to the outside of cancer cells and it can release anticancer drugs at proliferating and dividing stage of cancer cells, it can maximize anticancer effect of anticancer drugs.

The present invention was described above with reference to Examples and Experimental Examples, which is merely illustrative and those skilled in the art would know that various modifications and equivalent other embodiments are possible, understand. Therefore, the true scope of the present invention should be determined by technical features described in the following claims.

What is claimed is:

1. An anticancer agent comprising an anticancer drug-multi-walled carbon nanotube conjugate consisting of
    a multi-walled carbon nanotube, and
    an anticancer drug attached covalently thereto,
    wherein the anticancer drug is an amine compound and is covalently linked to the multi-walled carbon nanotube in a ratio of 23~35 wt % compared to total weight of the multi-walled carbon nanotube.

2. The anticancer agent according to claim 1, wherein the multi-walled carbon nanotube has diameter of 5 to 50 nm.

3. The anticancer agent according to claim 1, wherein the multi-walled carbon nanotube has length of 100 to 350 nm.

4. The anticancer agent according to claim 1, wherein the multi-walled carbon nanotube is modified to have at least one carboxylic group on the surface thereof.

5. The anticancer agent according to claim 1, the anticancer drug is covalently linked to the multi-walled carbon nanotube by attaching EDC (N-(3-Dimethylaminopropyl)-N-ethylcarbodiimide hydrochloride) linker to the multi-walled carbon nanotube at pH 5.2~5.5 and attaching the anticancer drug to the EDC linked multi-walled carbon nanotube at pH 5.9~6.2.

6. The anticancer drug according to claim 1, wherein the anticancer drug is doxorubicin, epirubicin, adriamycin, cisplatin, mitomycin-C or daunomycin.

7. The anticancer agent according to claim 1, further comprising epidermal growth factor (EGF).

8. The anticancer agent according to claim 1, wherein said anticancer drug is a drug for treating a cancer selected from a group consisting of liver cancer, colon cancer, cervical cancer, renal cancer, gastric cancer, prostate cancer, breast cancer, brain cancer, lung cancer, cervical cancer, colon cancer, bladder cancer, blood cancer and pancreatic cancer.

9. A pharmaceutical composition comprising:
    (a) a pharmaceutically effective amount of the anticancer agent according to claim 1; and
    (b) a pharmaceutically acceptable carrier.

10. A method for treating a subject suffering cancer, the method comprises administrating the anticancer agent according to claim 1.

11. The method according to claim 10, wherein the cancer is selected from a group consisting of liver cancer, colon cancer, cervical cancer, renal cancer, gastric cancer, prostate cancer, breast cancer, brain cancer, lung cancer, cervical cancer, colon cancer, bladder cancer, blood cancer and pancreatic cancer.

12. A drug delivery composition for delivering a drug to liver or lung tissue comprising a multi-walled carbon nanotube and a drug covalently bonded to the surface of the multi-walled carbon nanotube, wherein the drug is an amine compound and is covalently linked to the multi-walled carbon nanotube in a ratio of 23~35 wt % compared to total weight of the multi-walled carbon nanotube.

13. The drug delivery composition for delivering a drug to liver or lung tissue according to claim 12, wherein the drug is covalently linked to the multi-walled carbon nanotube by attaching EDC (N-(3-Dimethylaminopropyl)-N-ethylcarbodiimide hydrochloride) linker to the multi-walled carbon nanotube at pH 5.2~5.5 and attaching the anticancer drug to the EDC linked multi-walled carbon nanotube at pH 5.9~6.2.

14. The method according to claim 10, wherein the anticancer drug is released from covalently conjugated multi-walled carbon nanotube during late endosome and lysosome stage in a cancer cell after administration.

* * * * *